US010525071B2

(12) United States Patent
Wurtman et al.

(10) Patent No.: US 10,525,071 B2
(45) Date of Patent: *Jan. 7, 2020

(54) COMPOSITIONS CONTAINING PUFA AND METHODS OF USE THEREOF

(75) Inventors: Richard J. Wurtman, Boston, MA (US); Ingrid Richardson, Newton, MA (US)

(73) Assignee: MASSACHUSETS INSTITUE OF TECHNOLOGY, Cambridge, MA (US)

(*) Notice: Subject to any disclaimer, the term of this patent is extended or adjusted under 35 U.S.C. 154(b) by 736 days.

This patent is subject to a terminal disclaimer.

(21) Appl. No.: 11/920,914

(22) PCT Filed: May 23, 2006

(86) PCT No.: PCT/US2006/019766
§ 371 (c)(1),
(2), (4) Date: Nov. 21, 2007

(87) PCT Pub. No.: WO2006/127620
PCT Pub. Date: Nov. 30, 2006

(65) Prior Publication Data
US 2010/0099645 A1    Apr. 22, 2010

Related U.S. Application Data

(60) Provisional application No. 60/683,352, filed on May 23, 2006, provisional application No. 60/716,077, filed on Sep. 13, 2005, provisional application No. 60/755,058, filed on Jan. 3, 2006, provisional application No. 60/761,753, filed on Jan. 25, 2006.

(51) Int. Cl.
A61K 31/7072    (2006.01)
A61K 31/14      (2006.01)
A61K 31/202     (2006.01)
A61P 25/00      (2006.01)
A61P 25/28      (2006.01)
A61P 43/00      (2006.01)

(52) U.S. Cl.
CPC .......... *A61K 31/7072* (2013.01); *A61K 31/14* (2013.01); *A61K 31/202* (2013.01); *A61P 25/00* (2018.01); *A61P 25/28* (2018.01); *A61P 43/00* (2018.01)

(58) Field of Classification Search
None
See application file for complete search history.

(56) References Cited

U.S. PATENT DOCUMENTS

| 4,221,784 | A | | 9/1980 | Growdon et al. | |
|---|---|---|---|---|---|
| 4,810,497 | A | * | 3/1989 | Horrobin | 424/677 |
| 5,198,468 | A | | 3/1993 | Horrobin | |
| 5,492,899 | A | | 2/1996 | Masor et al. | |
| 5,977,174 | A | | 11/1999 | Bradley et al. | |
| 6,080,787 | A | | 6/2000 | Carlson et al. | |
| 6,509,178 | B1 | | 1/2003 | Tanaka et al. | |
| 6,989,376 | B2 | * | 1/2006 | Watkins et al. | 514/50 |
| 2002/0028787 | A1 | * | 3/2002 | Watkins et al. | 514/49 |
| 2002/0182196 | A1 | | 12/2002 | McCleary | |
| 2003/0044472 | A1 | | 3/2003 | Lang | |
| 2003/0114415 | A1 | | 6/2003 | Wurtman et al. | |
| 2004/0122094 | A1 | | 6/2004 | Saebo et al. | |
| 2004/0266874 | A1 | | 12/2004 | Akimoto et al. | |
| 2005/0027004 | A1 | | 2/2005 | Kyle et al. | |
| 2005/0096295 | A1 | * | 5/2005 | McMahon | A23C 9/1307 514/54 |
| 2006/0241077 | A1 | * | 10/2006 | Wurtman et al. | 514/49 |
| 2007/0004670 | A1 | * | 1/2007 | Wurtman et al. | 514/49 |
| 2010/0022567 | A1 | * | 1/2010 | Wurtman et al. | 514/274 |

FOREIGN PATENT DOCUMENTS

| AU | 768369 | 12/2003 |
|---|---|---|
| CN | 1435186 A | 8/2003 |
| DE | 19608137 | 9/1997 |
| EP | 0342795 | 11/1989 |
| EP | 0342795 A2 | 11/1989 |
| EP | 1302196 | 4/2003 |
| JP | 7143862 A | 6/1995 |
| JP | 9075000 A | 3/1997 |
| JP | 9285267 | 11/1997 |
| JP | 11-071274 A | 3/1999 |
| JP | 2004231585 | 8/2004 |
| NZ | 563659 | 5/2011 |
| WO | WO 94/28913 A1 | 12/1994 |

(Continued)

OTHER PUBLICATIONS

Testa et al., "Produrg Research: futile or fertile?" Biochemical Pharmacology (2004) vol. 68 pp. 2097-2106.*
Silverman, "The Organic Chemistry of Drug Design and Drug Action" Published 1992 by Academic Press, pp. 4-47.*
The Merck Manual of Diagnosis and Therapy, published 1999 by Merck Research Laboratories, pp. 1382-1383 and 1393-1400.*
Khedr et al., "Neural Matruation of Breastfed and Formula-fed Infants" Acta Pediatr (2004) vol. 93 pp. 734-738.*
Wurtman, "Synapse Formation and Cognitive Brain Development: effect of docosahexaenoic (DHA) and other dietary constituents" Metabolism (2008) vol. 57 suppl 2, S6-10.*
Wurtman et al., "Synaptic proteins and phospholipids are increased in gerbil brain by administering uridine plus docosahexaenoic acid orally" Brain Research (2006) vol. 1088, pp. 83-92.*

(Continued)

*Primary Examiner* — Eric Olson
(74) *Attorney, Agent, or Firm* — Mark S. Cohen; Pearl Cohen Zedek Latzer Baratz LLP

(57) ABSTRACT

This invention provides methods of increasing or enhancing the synthesis and levels of phospholipids, synapses, synaptic proteins, and synaptic membranes by a neural cell or brain cell; methods of treating a subject with a memory disorder, memory impairment, neurological disorder, or brain disease or disorder, comprising administering to the subject a composition comprising an omega-3 fatty acid, an omega-6 fatty acid, uridine, a metabolic precursor thereof, or a combination thereof.

24 Claims, 10 Drawing Sheets

(56) References Cited

FOREIGN PATENT DOCUMENTS

| | | |
|---|---|---|
| WO | WO 98/36745 | 8/1998 |
| WO | WO 00/06174 | 2/2000 |
| WO | WO 00/12102 | 3/2000 |
| WO | WO 01/84961 | 11/2001 |
| WO | WO 2002/023696 | 3/2002 |
| WO | WO 2002/089787 | 11/2002 |
| WO | WO 03/041701 | 5/2003 |
| WO | WO 2004/028529 | 4/2004 |
| WO | WO 2004/058160 | 7/2004 |
| WO | WO 2005/032271 | 4/2005 |
| WO | WO 2005/086619 | 9/2005 |
| WO | WO 2006/018314 | 2/2006 |
| WO | WO 2006/127620 | 11/2006 |

OTHER PUBLICATIONS

Cansev et al., "Chronic Administration of Docosahexaenoic Acid or Eicosapentaenoic Acid, but not Arachidonic Acid, Alone or in Combination With Uridine, Increases Brain Phosphatide and Synaptic Protein Levels in Gerbils" Neuroscience (2007) vol. 148 pp. 421-431.*

Full text of BPAI decision Ex Parte El Bakkouri, appeal 2009-012373, decided Jan. 15, 2010.*

Eastwood et al., "Synaptic pathology in the anterior cingulate cortex in schizophrenia and mood disorders. A review and a Western blot study of synaptophysin, GAP-43 and the complexins" Brain Research Bulletin (2001) vol. 55 No. 5 pp. 569-578.*

Visser et al., "Medial temporal lobe atrophy predicts Alzheimer's disease in patients with minor cognitive impairment" J Neurol Neurosurg Psychiatry 2002; vol. 72: pp. 491-497 (Year: 2002).*

Araki W. and Wurtman R. J. (1997) Control of membrane phosphatidylcholine biosynthesis by diacylglycerol levels in neuronal cells undergoing neurite outgrowth. Proc. Natl. Acad. Sci. USA 94, 11946-11950.

Babb S. M., Ke Y., Lange N., Kaufman M. J., Renshaw P. F., and Cohen B. M (2004) Oral choline increases choline metabolites in human brain. Psychiatry Res. 130, 1-9.

Cansev M., Watkins C. J., van der Beek E. M., Wurtman R. J. (2005) Oral Uridine 5' monophosphate (UMP) increases brain CDP-choline levels in gerbils. Brain Res. 1058, 101-108.

Cansev M. and Wurtman R. J. (2005) Exogenous cytidine-5'-diphosphocholine increases brain cytidine-5'-diphosphocholine levels in gerbils, 20th Biennial Meeting of the ISNESN Abstracts, Aug. 21-26, 2005, Innsbruck, Austria, J. Neurochem. 94 (Supp. 2), 105-106.

Cao D., Xue R., Xu J., and Liu Z. (2005) Effects of docosahexaenoic acid on the survival and neurite outgrowth of rat cortical neurons in primary cultures. J. Nutr. Biochem. 16, 538-546.

Cohen E. L. and Wurtman R. J. (1976) Brain acetylcholine: control by dietary choline. Science 191, 561-562.

Coleman P., Federoff H., and Kurlan R. (2004) A focus on the synapse for neuroprotection in Alzheimer disease and other dementias. Neurology 63, 1155-1162.

Cornford E. M., Braun L. D., and Oldendorf W. H. (1978) Carrier mediated blood-brain barrier transport of choline and certain choline analogs. J. Neurochem. 30, 299-308.

Fenton WS, Dickerson F, Boronow J, Hibbeln JR, Knable M. (2001) A placebo-controlled trial of omega-3 fatty acid (ethyl eicosapentaenoic acid) supplementation for residual symptoms and cognitive impairment in schizophrenia. Am J Psychiatry. December;158(12):2071-4.

Ferreira A. and Rapoport M. (2002) The synapsins: beyond the regulation of neurotransmitter release. Cell. Mol. Life Sci. 59, 589-595.

Folch J., Lees M., and Sloane-Stanley G. H. (1957) a simple method for the isolation and purification of total lipides from animal tissues, J. Biol Chem. 226, 497-509.

Fujita A. and Kurachi Y. (2000) SAP family proteins. Biochem. Biophys. Res. Commun. 269, 1-6.

Genchev D. D. and Mandel P. (1974) CTP synthetase activity in neonatal and adult rat brain. J. Neurochem. 22, 1027-1030.

Harris W. S. (2005) Omega-3 fatty acids, in Encyclopedia of Dietary Supplements, (Coates P. M., Blackman M. R., Cragg G. M., Levine M., Moss J. and White J. D., eds), pp. 493-504. Marcel Dekker, New York.

Hashimoto M., Hossain S., Shimada T., Sugioka K., Yamasaki H., Fujii Y., Ishibashi Y., Oka J-I., and Shido O. (2002) Docosnahexaenoic acid provides protection from impairment of learning ability in Alzheimer's disease model rats. J. Neurochem. 81, 1084-1091.

Kennedy E. M. and Weiss S. B. (1956) The function of cytidine coenzymes in the biosynthesis of phospholipids. J. Biol. Chem. 222, 193-214.

Knapp S. and Wurtman R. J. (1999) Enhancement of free fatty acid incorporation into phospholipids by choline plus cytidine. Brain Res. 822, 52-59.

Labarca C. and Paigen K. (1980) A simple, rapid and sensitive DNA assay procedure. Anal. Biochem. 102, 344-352.

Lee V., Trojanowsky J. Q. and Schlaepfer W. W. (1982) Induction of neurofilament triplet proteins in PC12 cells by nerve growth factor. Brain Res. 238, 169-180.

Li J. Y., Boado R. J., and Pardridge W. M. (2001) Cloned blood-brain barrier adenosine transporter is identical to the rat concentrative Na+ nucleoside cotransporter CNT2. J Cereb. Blood Flow Metab. 21, 929-936.

Lopez-Coviella I., Agut J., Savci V., Ortiz J. A., and Wurtman R. J. (1995) Evidence that 5'-Cytidinediphosphocholine can affect brain phospholipid composition by increasing choline and cytidine plasma levels. J. Neurochem. 65, 889-894.

Marszalek J. R., Kitidis C., DiRusso C. C., and Lodish H. F. (2005) Long-chain acyl-Coa synthetase 6 preferentially promotes DHA metabolism. J. Biol. Chem. 280, 10817-10826.

Marszalek J. R. and Lodish H. F. (2005) Docosahexaenoic acid, fatty acid-interacting proteins, and neuronal function: breastmilk and fish are good for you. Ann. Rev, Cell Dev. Biol. 21, 633-657.

McCann J, C. and Ames B. N. (2005) Is docosahexaenoic acid, an n-3 long-chain polyunsaturated fatty acid, required for development of normal brain function? An overview of evidence from cognitive and behavioral tests in humans and animals. Am., J.Clin. Nutr. 82, 281-295.

Millington W. R. and Wurtman R. J. (1982) Choline administration elevates brain phosphorylcholine concentrations. J. Neurochem. 38, 1748-1752.

Nitsch R. M., Blusztajn J. K., Pittas A. G., Slack B. E., Growdon J. H., and Wurtman R. J, (1992) Evidence for a membrane defect in Alzheimer disease brain. Proc. Natl. Acad. Sci. USA 89, 1671-1675.

Pooler A, M., Guez D. H., Benedictus R., and Wurtman R. J. (2005) Uridine enhances neurite outgrowth in nerve growth factor-differentiated pheochromocytoma cells. Neuroscience 134, 207-214.

Rapoport S. I. (2001) In vivo fatty acid incorporation into brain phospholipids in relation to plasma availability, signal transduction and membrane remodeling. J. Mol. Neurosci. 16, 243-261.

Richardson U.I., Watkins C.J., Pierre C., Ulus I.H., and Wurtman R.J. (2003) Stimulation of CDP-choline synthesis by uridine or cytidine in PC12 rat pheochromocytoma cells. Brain Res. 971, 161-167.

Ross B. M., Moszczynska A., Blusztajn J. K., Sherwin A., Lozano A., and Kish S. J. (1997) Phospholipid biosynthetic enzymes in human brain. Lipids 32, 351-358.

(56) References Cited

OTHER PUBLICATIONS

Selkoe D, J. (2002) Alzheimer's disease is a synaptic failure. *Science* 298, 789-791.
Artemis P. Simopoulos, Alexander Leaf, Norman Salem, Jr. (1999) Essentiality of and Recommended Dietary Intakes for Omega-6 and Omega-3 Fatty Acids. *Annals of Nutrition & Metabolism*; 43:127-130.
Soderberg M., Edlund C., Kristensson K., and Dallner G. (1991) Fatty acid composition of brain phosholipids in aging and in Alzheimer's disease. *Lipids* 26, 421-425.
Spanner S. and Ansell G. B. (1979) Choline kinase and ethanolamine kinase activity in the cytosol of nerve endings from rat forebrain. *Biochem. J.* 110, 201-206.
Spector A. A. (2001) Plasma free fatty acid and lipoproteins as sources of polyunsaturated fatty acid for the brain. *J. Mol. Neurosci.* 16, 159-165.
Stalenhoef A. F. H., DeGraaf J., Wittekoek M. E., Bredie S. J. H., Demacker P. N. M. and Kastelein J. J. P. (2000) The effect of concentrated n-3 fatty acids versus gemfibrozil on plasma lipoproteins, low density lipoprotein heterogeneity and oxidizability in patients with hypertriglyceridemia. *Atherosclerosis* 153, 129-138.
Suzuki N. N., Koizumi K., Fukushima M., Matsuda A., and Inagaki F. (2004) Structural basis for the specifity, catalysis, and regulation of human uridine-cytidine kinase. *Structure* 12, 751-764.
Svanborg A. and Svennerholm L. (1961) Plasma total lipids, cholesterol, triglycerides, phospholipids and free fatty acids in a healthy Scandinavian population. *Acta Med. Scand.* 169, 43-49.
Teather L. A. and Wurtman R. J. (2003) Dietary cytidine (5')-diphosphocholine supplementation protects against development of memory deficits in aging rats. *Prog. Neuropsychopharmacol Biol Psychiatry* 27, 711-717.
Teather L. A. and Wurtman R. J. (2005) Dietary CDP-choline supplementation prevents memory impairment caused by impoverished environmental conditions in rats. *Learn. Mem.* 12, 39-43.
Terry R. D., Masliah E., Salmon D. P., Butters N., DeTeresa R., Hill R., Hansen L. A., and Katzman R. (1991) Physical basis of cognitive alterations in Alzheimer's disease: Synapse loss is the major correlate of cognitive impairment. *Ann. Neurol.* 30, 572-580.
Ulus I. H., Wurtman R. J., Mauron C. and Blusztajn J. K. (1989) Choline increases acetylcholine release and protects against the stimulation-induced decrease in phosphatide levels within membranes. *Brain Res.* 484, 217-227.
Wang L., Pooler A. M., Regan M. A. and Wurtman R. J. (2004) Uridine increases neurotransmitter release in aged rats. 34th Society for Neuroscience Abstracts, Oct. 23-27, San Diego, CA, USA.
Wang L., Pooler A. M., Regan M. A. and Wurtman R. J. (2005) Dietary uridine-5'-monophosphate supplementation increases potassium-induced dopamine release and promotes neurite outgrowth in aged rats. *J. Mol. Neurosci.* 27, 137-146.
Wurtman R. J., Regan M., Ulus I., and Yu L. (2000) Effect of oral CDP-choline on plasma choline and uridine levels in humans. *Biochem. Pharmacol.* 60, 989-992.
Vyh Yu. (2002) Scientific rationale and benefits of nucleotide supplementation of infant formula. *J. Pediatr. Child Health* 38, 543-549.
Carlezon W.A. et al (2005) "Antidepressant-like Effects of Uridine and Omega-3 Fatty Acids are Potentiated by Combined Treament in Rats" Biol Psychiatry 2005, 57;343-350.
Willatts P et al (1998) "Effect of long-chain polyunsaturated fatty acids in infant formula on problem solving at 10 months of age" The Lancet, vol. 352.
Champoux M. et al (2002) "Fatty Acid Formula Supplementation and Neuromotor Development in Rhesus Monkey Neonates" Pediatric Research, vol. 51, No. 3.
Carlson S. E. et al (1996) "A Randomized Trial of Visual Attention of Preterm Infants Fed Docosahexaenoic Acid Until Two Months" Lipids, vol. 31 No. 1.
Birch E.E. et al (2000) "A randomized controlled trial of early dietary supply of long-chain polyunsaturated fatty acids and mental development in term infants" Developmental Medicine & Child Neurology, 42: 174-181.
Solfizzi V. et al (2005) "Dietary fatty acids intake: possible role in cognitive decline and dementia" Experimental Gerontology 40, 257-270.
Lim Giselle P. et al (2005) "A Diet Enriched with the Omega-3 Fatty Acid Docosahexaenoic Acid Reduces Amyloid Burden in an Aged Alzheimer Mouse Model" The Journal of Neuroscience, Mar. 23, 2005—25(12):3032-3040.
MacLean C. H. et al (2005) "Effects of Omega-3 fatty Acids on Cognitive Funxtion with Aging, Dementia, and Neurological Diseases" AHRQ Publication No. 05-E011-2, Feb. 2005.
Morris M. C. et al (2003) "Consumption of Fish and n-3 Fatty Acids and Risk of Incident Alzheimer Disease" Arch Neurol, vol. 60.
Agut J, Ortiz JA. "Age-related changes in memory and their pharmacologic modulation" Ann N Y Acad Sci. 1991;640;295-7. PMID: 1776755.
De la Morena E. "Efficacy of CDP-choline in the treatment of senile alterations in memory". Ann N Y Acad Sci. 1991;640:233-6. PMID: 1776744.
Mosharrof AH, Petkov VD, Petkov VV. "Effects of meclofenoxate and citicholine on learning and memory in aged rats" Acta Physiol Pharmacol Bulg. 1987;13(4):17-24. PMID: 3129903.
Lozano Fernandez R. "Efficacy and safety of oral CDP-choline. Drug surveillance study in 2817 cases". Arzneimittelforschung. 1983;33(7A):1073-80. PMID: 6684470.
Crawford et al. www.thelancet.com vol. 33, Aug. 27, 2005.
Fischer et al. Arachidonate has Protumor—Promoting Action that is Inhibited by Linoleate in Mouse Skin Carcinogenesis, The Journal of Nutrition, Apr. 1996, 126, 4S, Research Library Core, p. 1099S.
Belikov V.G. "General Pharmaceutical Chemistry" in two parts. Part 1. Moscow, "Vysshaya shkola", 1993, chapter 2.2, p. 43-47.
Kazimirko V.K. et al. "Function of unsaturated fatty acids in the organism"// Zdorov'ya Ukraini, No. 95, May 2004. [on-line] [Found on Jan. 19, 2010] found from the Internet: http://health-ua.com/articles/716.html.
Rodriguez-Cruz M et al. "Molecular mechanisms of action and health benefits of polyunsaturated fatty acids". Rev Invest Clin May-Jun. 2005; 57(3):457-72, abstract [found Jul. 6, 2010], found from PubMed PDIM: 16187707.
Schmidt R. Et al. "Human Physiology" in 3 volumes, vol. 1, Moscow, "Mir", 1996, p. 51, 54, 57-58.
Valenzuela A et al. "Docosahexaenoic acid (DHA) in fatal development and in infant nutrition". Rev Med Chil. Oct. 2001; 129(10):1203-11 found on Jan. 29, 2010 from PubMed PMID: 11775350.
Yehuda S et al. "Modulation of learning, pain thresholds, and thermoregulation int he rat by preparations of free putrified alpha-linolenic and linoleic acids: determination of the optimal omega 3-to-omega 6 ratio". Proc Natl Acad Sci USA. Nov. 1, 1993; 90(21):10345-9, abstract, found on Jan. 25, 2010 from PubMed PMID: 7901853.
Zakharov V.V. et al. "Syndrome of moderate cognitive disorders in elderly age: diagnosis and treatment"// "Russian Medical Journal", May 29, 2004, vol. 12, No. 10 [on-line] [Found on Jan. 19, 2010] found from the Internet: http://www.rmj.ru/articles_313.htm.
Fat Emulsions in Parenteral Feeding. Proceedings of the Congress of the European Association of Enteral and Parenteral Feeding in 2004// "Khirurgiya", vol. 07/N Feb. 2005 [on-line] [Found on Jan. 18, 2010] found from the Internet: http://old.consilium-medicum.com/media/surgery/05_02/42.shtml.
"Synaptogenesis"// post on a website "Peoples' Friendship University of Russia" in chapter "Glossary" [on-line] [Found on Aug. 25, 2010] found from the Internet: http://www.humanities.edu.ru/db/msg/72534.
Simopoulos A.P. et al., Workshop on the Essentiality of and Recommended Dietary Intakes for Omega-6 and Omega-3 Fatty Acids: Journal of the American College of Nutrition, 1999, vol. 18, No. 5, pp. 487-489.

(56) References Cited

OTHER PUBLICATIONS

Whalley L.J. et al., "Cognitive Aging, Childhood Intelligence, and the Use of Food Supplements: Possible Involvement of n-3 Fatty Acids" The American Journal of Clinical Nutrition, 2004, vol. 80, No. 6, pp. 1650-1657.
Favrelière S. et al., "DHA-enriched phspholipid diets modulate age-related alterations in rat hippocampus," Neurobiology of Aging, vol. 24, pp. 233-243, 2003.
Sun-Young Lim et al., "Intakes of Dietary Docosahexaenoic Acid Ethyl Ester and Egg Phosphatidylcholine Improve Maze-Learning Ability in Young and Old Mice," the Journal of Nutrition, vol. 130, pp. 1629-1632, 2000.
Terano T. et al., "Docosahexaenoic Acid Supplementation Improves the Moderately Severe Dementia from Thrombotic Cerebrovascular Diseases," Lipids, vol. 34, pp. S345-S346, 1999.
Fioravanti M, Yanagi M. Cytidinediphosphocholine (CDP-choline) for cognitive and behavioural disturbances associated with chronic cerebral disorders in the elderly. Cochrane Database of Systematic Reviews 2005, Issue 2.
English translation of Office Action of corresponding Chinese Patent Application No. 200680026945.4, dated Sep. 15, 2011.
Office Action of corresponding New Zealand Patent Application No. 563660 dated Oct. 21, 2011.
Wurtman et al., Synaptic Proteins and Phospholipids are Increased in Gerbil Brain by Administering Uridine Plus Docosahexaenoic Acid Orally, Brain Research, 2006, vol. 99, pp. 83-92.
Wurtman et al., Administration of Docosahexaenoic Acid, Uridine and Choline Increases Levels of Synaptic Membranes and Dendritic Spines in Rodent Brain, World Rev Nutr Diet. Basel, Karger, 2009, vol. 99, pp. 71-96.
Wurtman et al., Efficacy of a Medical Food in Mild Alzheimer's Disease: A Randomized, Controlled Trial, Alzheimer's & Dementia, 2010, vol. 6, pp. 1-10.
Foot, M., et al., "Influence of dietary fat on the lipid composition of rat brain synaptosomal and microsomal membranes," 1982, Biochemical Journal, vol. 208, pp. 631-640.
Garcia, MC, et al., "Effect of Docosahexaenoic Acid on the Synthesis of Phosphatidylserine in Rat Brain Microsomes and C6 Glioma Cells," Journal of Neurochemistry, 1998, vol. 70, iss. 1, pp. 24-30.
Gazzah, N., et al., "Decrease of brain phspholipid synthesis in free-moving n-3 fatty acid defiant rats," 1995, Journal of Neurochemistry, vol. 64, iss. 2, pp. 908-918.
Anderson, J.W. et al., "Breast-feeding and cognitive development: a meta-analysis," Am J Clin Nutr, Oct. 1999 vol. 70 No. 4, pp. 525-535.
Caamaño J. et al., "Effects of CDP-choline on cognition and cerebral hemodynamics in patients with Alzheimer's disease," Methods Find Exp Clin Pharmacol. Apr. 1994;16(3):211-8.
Cacabelos, R. et al., "Therapeutic Effects of CDP-Choline in Alzheimer's Disease Cognition, Brain Mapping, Cerebrovascular Hemodynamics, and Immune Factors," Annals of the New York Academy of Sciences, vol. 777, The Neurobiology of Alzheimer's Disease, pp. 399-403, Jan. 1996.
Carlezon, W. A. Jr., "Antidepressant-like Effects of Uridine and Omega-3 Fatty Acids are Potentiated by Combined Treatment in Rats," Biol. Psychiatry, 2005, vol. 57, No. 4, pp. 343-350.
Decsi T et al., "N-3 Fatty Acids and Pregnancy Outcomes," Current Opinion in Clinical Nutrition and Metabolic Care, Mar. 2005, vol. 8, No. 2, pp. 161-166, Abstract.
Helland I. B. et al.: "Maternal Supplementation with Very-Long-Chain n-3 Fatty Acids During Pregnancy and Lactation Augments Children's IQ at 4 Years of Age" Pediatrics, 2003, vol. 111, No. 1, pp. e39-e44.
Horwood, L.J. et al., "Breast milk feeding and cognitive ability at 7-8 years," Arch Dis Child Fetal Neonatal Ed 2001; 84, pp. F23-F27.
Uauy, R. et al., "Breast is best: human milk is the optimal food for brain development," Am J Clin Nutr, Oct. 1999, vol. 70 No. 4, pp. 433-434.
Simopoulos et al., "Workshop on the Essentiality of and Recommended Dietary Intakes for Omega-6 and Omega-3 Fatty Acids, "Journal of the American College of Nutrition, 1999, vol. 18, No. 5, pp. 487-489.
Whalley et al., "Cognitive Aging, Childhood Intelligence, and the Use of Food Supplements: Possible Involvement of n-3 Fatty Acids," The American Journal of Clinical Nutrition, 2004, vol. 80, No. 6, pp. 1650-1657.
Office Action for Australian Patent Appln. No. 2014274585 dated Sep. 21, 2016.
Breast feeding increases choline which means more brain cells [retrieved from the internet on Sep. 20, 2017 <URL: http://www.news-medical.net/news/2004/03/22/63.aspx> published Mar. 22, 2014 as per the documentBreast feeding increases choline which means more brain cells.
Baumgartner C.Breast feeding increases choline which means more brain cells "Psychomotor and social development of breast-fed and bottle-fed babies during their first year of life" Acta Paediatr Hung. 1984 vol. 25 No. 4, pp. 409-417.
Office Action for Canadian Application No. 2645647 dated Nov. 28, 2014.
Office Action for Japanese Patent Application No. 2008-513592 dated Nov. 6, 2012.
Calderon et al., Docosahexaenoic acid promotes neutrite growth in hippocampal neurons, 2004, Journal of Neurochemistry, vol. 90, No. 4, p. 979-988.
Office Action for Japanese 2008-513596 dated Nov. 6, 2012.
Wilde et al. "Dietary fatty acids alter blood pressure, behaviou and brain membrane composition of hypertensive rates" Brain Res., 2003, vol. 988, No. 1-2, pp. 9-19.
Coviella et. al., Effect of orally administered cytidine 5'-diphosphate choline on brain phospholipid content, 1992, Journal of Nutritional Biochemistry, vol. 3, No. 6 p. 313-315.
Office Action European application No. 06 770 862.8 dated Jan. 27, 2016.
U.S. Office Action dated Jun. 17, 2014.

* cited by examiner

US 10,525,071 B2

COMPOSITIONS CONTAINING PUFA AND METHODS OF USE THEREOF

GOVERNMENT INTEREST STATEMENT

The invention described herein was made in whole or in part with government support under Grant No. MH028783 awarded by the National Institutes of Health. The government has certain rights in this invention.

FIELD OF INVENTION

This invention provides methods of increasing or enhancing the synthesis and levels of phospholipids, synapses, synaptic proteins, and synaptic membranes by a neural cell or brain cell; methods of treating a subject with a memory disorder, memory impairment, neurological disorder, or brain disease or disorder, comprising administering to the subject a composition comprising an omega-3 fatty acid, an omega-6 fatty acid, uridine, a metabolic precursor thereof, or a combination thereof.

BACKGROUND OF THE INVENTION

Dementia is a brain disorder that seriously affects a person's ability to carry out daily activities. The most common form of dementia among older people is Alzheimer's disease (AD), which initially involves the parts of the brain that control thought, memory, and language. A decline in memory and cognitive (thinking) function is considered by many authorities to be a normal consequence of aging. People with ARCD experience deterioration in memory and learning, attention and concentration, thinking, use of language, and other mental functions. Methods of treating these diseases and disorders are urgently needed in the art.

SUMMARY OF THE INVENTION

This invention provides methods of increasing or enhancing the synthesis and levels of phospholipids, synapses, synaptic proteins, and synaptic membranes by a neural cell or brain cell; methods of treating a subject with a memory disorder, memory impairment, neurological disorder, or brain disease or disorder, comprising administering to the subject a composition comprising an omega-3 fatty acid, an omega-6 fatty acid, uridine, a metabolic precursor thereof, or a combination thereof.

In one embodiment, the present invention provides a method of increasing an amount of a synaptic membrane of a neural cell or brain cell of a subject with an age-related memory disorder, comprising administering to the subject an omega-3 fatty acid or a metabolic precursor thereof, thereby increasing an amount of a synaptic membrane of a neural cell or brain cell of a subject with an age-related memory disorder.

In another embodiment, the present invention provides a method of increasing an amount of a synaptic membrane of a neural cell or brain cell of a subject with an age-related memory disorder, comprising administering to the subject an omega-6 fatty acid or a metabolic precursor thereof, thereby increasing an amount of a synaptic membrane of a neural cell or brain cell of a subject with an age-related memory disorder.

In another embodiment, the present invention provides a method of increasing an amount of a synaptic membrane of a neural cell or brain cell of a subject with an age-related memory disorder, comprising administering to the subject a composition comprising: (a) a uridine, an acyl derivative thereof, a uridine phosphate, or a CDP-choline; and (b) an omega-3 fatty acid or a metabolic precursor thereof, thereby increasing an amount of a synaptic membrane of a neural cell or brain cell of a subject with an age-related memory disorder.

In another embodiment, the present invention provides a method of increasing an amount of a synaptic membrane of a neural cell or brain cell of a subject with an age-related memory disorder, comprising administering to the subject a composition comprising: (a) a uridine, an acyl derivative thereof, a uridine phosphate, or a CDP-choline; and (b) an omega-6 fatty acid or a metabolic precursor thereof, thereby increasing an amount of a synaptic membrane of a neural cell or brain cell of a subject with an age-related memory disorder.

In another embodiment, the present invention provides a method of treating a subject with Alzheimer's disease, memory impairment, or memory loss, comprising administering to the subject an omega-3 fatty acid or a metabolic precursor thereof, whereby the omega-3 fatty acid or metabolic precursor thereof increases a synthesis of a phospholipid by the neural cell, thereby treating a subject with Alzheimer's disease, memory impairment, or memory loss.

In another embodiment, the present invention provides a method of treating a subject with Alzheimer's disease, memory impairment, or memory loss, comprising administering to the subject an omega-6 fatty acid or a metabolic precursor thereof, whereby the omega-6 fatty acid or metabolic precursor thereof increases a synthesis of a phospholipid by the neural cell, thereby treating a subject with Alzheimer's disease, memory impairment, or memory loss.

In another embodiment, the present invention provides a method of treating a subject with Alzheimer's disease, memory impairment, or memory loss, comprising administering to the subject a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by the neural cell, thereby treating a subject with Alzheimer's disease, memory impairment, or memory loss.

In another embodiment, the present invention provides a method of treating a subject with Alzheimer's disease, memory impairment, or memory loss, comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by the neural cell, thereby treating a subject with Alzheimer's disease, memory impairment, or memory loss.

In another embodiment, the present invention provides a method of treating a subject with a memory disorder selected from Pick's disease, Lewy Body disease, Huntington's disease and minimal cognitive impairment (MCI), comprising administering to the subject an omega-3 fatty acid or a metabolic precursor thereof, whereby the omega-3 fatty acid or metabolic precursor thereof increases a synthesis of a phospholipid by the neural cell, treating a subject with a memory disorder selected from Pick's disease, Lewy Body disease, Huntington's disease and MCI.

In another embodiment, the present invention provides a method of treating a subject with a memory disorder selected from Pick's disease, Lewy Body disease, Huntington's disease and MCI, comprising administering to the subject an omega-6 fatty acid or a metabolic precursor thereof, whereby the omega-6 fatty acid or metabolic precursor thereof increases a synthesis of a phospholipid by the neural cell, thereby treating a subject with a memory disorder selected from Pick's disease, Lewy Body disease, Huntington's disease and MCI.

In another embodiment, the present invention provides a method of treating a subject with a memory disorder selected from Pick's disease, Lewy Body disease, and Huntington's disease, comprising administering to the subject a composition comprising (a) a uridine, an acyl derivative thereof, a uridine phosphate, or a CDP-choline; and (b) an omega-3 fatty acid or a metabolic precursor thereof, whereby the composition increases a synthesis of a phospholipid by the neural cell, thereby treating a subject with a memory disorder.

In another embodiment, the present invention provides a method of treating a subject with a memory disorder selected from Pick's disease, Lewy Body disease, and Huntington's disease, administering to the subject a composition comprising (a) a uridine, an acyl derivative thereof, a uridine phosphate, or a CDP-choline; and (b) an omega-6 fatty acid or a metabolic precursor thereof, whereby the composition increases a synthesis of a phospholipid by the neural cell, thereby treating a subject with a memory disorder.

In another embodiment, the present invention provides a method of increasing a size or number of synapses in a brain of a subject with an age-related memory disorder, comprising administering to the subject an omega-3 fatty acid or a metabolic precursor thereof, thereby increasing a size or number of synapses in a brain of a subject with an age-related memory disorder.

In another embodiment, the present invention provides a method of increasing a size or number of synapses in a brain of a subject with an age-related memory disorder, comprising administering to the subject an omega-6 fatty acid or a metabolic precursor thereof, thereby increasing a size or number of synapses in a brain of a subject with an age-related memory disorder.

In another embodiment, the present invention provides a method of increasing a size or number of synapses in a brain of a subject with an age-related memory disorder, comprising administering to the subject a composition comprising: (a) a uridine, an acyl derivative thereof, a uridine phosphate, or a CDP-choline; and (b) an omega-3 fatty acid or a metabolic precursor thereof, thereby increasing a size or number of synapses in a brain of a subject with an age-related memory disorder.

In another embodiment, the present invention provides a method of increasing a size or number of synapses in a brain of a subject with an age-related memory disorder, comprising administering to the subject a composition comprising: (a) a uridine, an acyl derivative thereof, a uridine phosphate, or a CDP-choline; and (b) an omega-6 fatty acid or a metabolic precursor thereof, thereby increasing a size or number of synapses in a brain of a subject with an age-related memory disorder.

In another embodiment, any of the methods and compositions of the present invention comprises administration of an omega-3 fatty acid and a choline. In another embodiment, any of the methods and compositions of the present invention comprise administration of an omega-3 fatty acid and a choline salt. In another embodiment, any of the methods and compositions of the present invention comprises administration of an omega-6 fatty acid and a choline. In another embodiment, any of the methods and compositions of the present invention comprises administration of an omega-6 fatty acid and a choline salt.

In another embodiment, any of the methods and compositions of the present invention comprises administration of a composition comprising an omega-3 fatty acid, a uridine, and a choline. In another embodiment, any of the methods and compositions of the present invention comprises administration of composition comprising an omega-3 fatty acid, a uridine, and a choline salt. In another embodiment, any of the methods and compositions of the present invention comprises administration of a composition comprising an omega-6 fatty acid, a uridine, and a choline. In another embodiment, any of the methods and compositions of the present invention comprises administration of composition comprising an omega-6 fatty acid, a uridine, and a choline salt.

In another embodiment, any of the methods and compositions of the present invention comprises administration of an omega-6 fatty acid and an omega-3 fatty acid. In another embodiment, any of the methods and compositions of the present invention comprises administration of an omega-6 fatty acid, an omega-3 fatty acid, and a uridine. In another embodiment, any of the methods and compositions of the present invention comprises administration of an omega-6 fatty acid, an omega-3 fatty acid, and a choline. In another embodiment, any of the methods and compositions of the present invention comprises administration of an omega-6 fatty acid, an omega-3 fatty acid, and a choline salt. In another embodiment, any of the methods and compositions of the present invention comprises administration of an omega-6 fatty acid, an omega-3 fatty acid, a uridine, and a choline. In another embodiment, any of the methods and compositions of the present invention comprises administration of an omega-6 fatty acid, an omega-3 fatty acid, a uridine, and a choline salt.

DETAILED DESCRIPTION OF THE INVENTION

Figure 1:
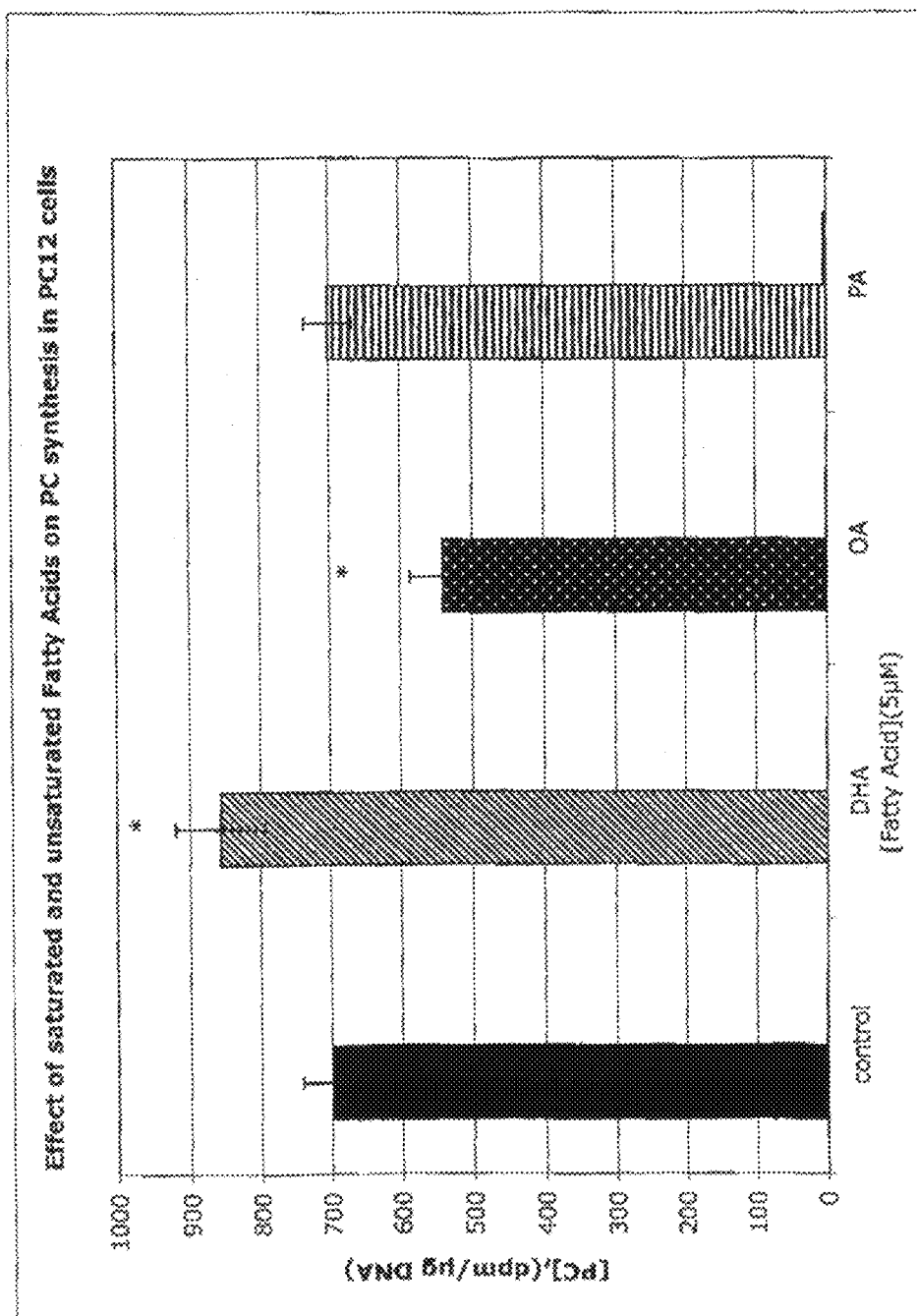
FIG. 1: DHA increases phospholipid synthesis in PC12 cells. PC12 cells were incubated overnight in with fatty acids, then incubated in media containing $^{14}$C-labeled choline. Graph depicts incorporation of $^{14}$C label into phosphatidylcholine in disintegrations per minute (dpm) per microgram (μg) DNA. DHA: docosahexaenoic acid. OA: oleic acid. PA: palmitic acid. *-p<0.05.

This invention provides methods of increasing or enhancing the synthesis and levels of phospholipids, synapses, synaptic proteins, and synaptic membranes by a neural cell or brain cell; methods of treating a subject with a memory disorder, memory impairment, neurological disorder, or brain disease or disorder, comprising administering to the subject a composition comprising an omega-3 fatty acid, an omega-6 fatty acid, uridine, a metabolic precursor thereof, or a combination thereof.

In another embodiment, the present invention provides a method of increasing a level of a phospholipid of a neural cell of a subject, comprising administering to the subject an omega-3 fatty acid or a metabolic precursor thereof, thereby increasing a level of a phospholipid of a neural cell of a subject. In another embodiment, the subject has a memory disorder. In another embodiment, the disorder is age-related. Each possibility represents a separate embodiment of the present invention.

In another embodiment of methods and compositions of the present invention, an omega-3 fatty acid, omega-6 fatty acid, uridine, choline, choline salt, or combination thereof is administered in a pharmaceutical composition.

In another embodiment of methods and compositions of the present invention, a composition that is administered increases a synthesis of a phospholipid by a neural cell or brain cell of the subject. In another embodiment, an omega-3 fatty acid increases a synthesis of a phospholipid by a neural cell or brain cell of the subject. In another embodiment, an omega-6 fatty acid increases a synthesis of a phospholipid by a neural cell or brain cell of the subject. In another embodiment, a uridine, an acyl derivative thereof, a uridine phosphate, or a CDP-choline increases a synthesis of a phospholipid by a neural cell or brain cell of the subject. In another embodiment, a choline increases a synthesis of a phospholipid by a neural cell or brain cell of the subject. In another embodiment, a choline salt increases a synthesis of a phospholipid by a neural cell or brain cell of the subject. Each possibility represents a separate embodiment of the present invention.

In another embodiment, the present invention provides a method of increasing a level of a phospholipid of a brain cell of a subject, comprising administering to the subject an omega-3 fatty acid or a metabolic precursor thereof, thereby increasing a level of a phospholipid of a brain cell of a subject. In another embodiment, the subject has a memory disorder. In another embodiment, the disorder is age-related. Each possibility represents a separate embodiment of the present invention.

In another embodiment, the present invention provides a method of increasing or enhancing a synthesis of a phospholipid by a neural cell or brain cell of a subject, comprising administering to the subject an omega-3 fatty acid or a metabolic precursor thereof, thereby increasing or enhancing a synthesis of a phospholipid by a neural cell or brain cell of a subject. In another embodiment, the subject has a memory disorder. In another embodiment, the disorder is age-related. Each possibility represents a separate embodiment of the present invention.

As provided herein, the results presented in Examples 1 and 5 demonstrate that administration of docosahexaenoic acid (DHA), an omega-3 fatty acid, to neural and brain cells increases their phospholipid synthesis, as evidenced by increased incorporation of labeled choline. Omega-3 fatty acid administration increased synthesis of total phospholipids, phosphatidylcholine, and phosphatidylethanolamine (Example 2), showing that the effect is not limited to particular phospholipids. PC12 cells display differentiated functions of neuronal cells and are commonly used in the art as a cell line model of neuronal cells. The results presented in Example 11 show that omega-3 fatty acids increase phospholipid synthesis in neurons in short-term culture.

In another embodiment, the present invention provides a method of increasing an amount of a synaptic membrane of a neural cell or brain cell of a subject, comprising administering to the subject an omega-3 fatty acid or a metabolic precursor thereof, thereby increasing an amount of a synaptic membrane of a neural cell or brain cell of a subject. In another embodiment, the subject has a memory disorder. In another embodiment, the disorder is age-related. Each possibility represents a separate embodiment of the present invention.

The phospholipid that is increased by methods and compositions of the present invention is, in another embodiment, a phosphatidic acid. The term "phosphatidic acid" is, in another embodiment, synonymous with the term "phosphatide." In another embodiment, the phospholipid is a phosphatidylcholine ("PC"; Example 1). In another embodiment, the phospholipid is a phosphatidylethanolamine ("PE"; Example 2). In another embodiment, the phospholipid is a phosphatidylserine ("PS"). In another embodiment, the phospholipid is a phosphatidylinositol ("PI"). In another embodiment, the phospholipid is sphingomyelin. In another embodiment, the phospholipid is a phosphoglyceride. In another embodiment, the phospholipid is any other phospholipid known in the art. Each possibility represents a separate embodiment of the present invention.

In another embodiment, PI, greatly increased by methods of the present invention, acts as a reservoir of 1 or more second messenger molecules. In another embodiment, the second messenger molecule is inositol 1,4,5-trisphosphate ($IP_3$). In another embodiment, the second messenger molecule is diacylglycerol (DAG). In another embodiment, protein kinase C (PKC) signaling is increased by methods and compositions of the present invention. In another embodiment, a signaling pathway downstream of $IP_3$ is activated by methods and compositions of the present invention. In another embodiment, intracellular calcium levels are increased by methods and compositions of the present invention. In another embodiment, a signaling pathway downstream of DAG is activated by methods and compositions of the present invention. In another embodiment, a signaling pathway downstream of PKC is activated by methods and compositions of the present invention. In another embodiment, a signaling pathway downstream of intracellular calcium is activated by methods and compositions of the present invention.

In another embodiment, sphingomyelin, increased by methods and compositions of the present invention acts as a source of ceramide. Each possibility represents a separate embodiment of the present invention.

In another embodiment, DHA and/or UMP in methods and compositions of the present invention act as bulk precursors of cellular phospholipids. In another embodiment, UMP acts by activating P2Y receptors for UMP formed from uridine. In another embodiment, DHA acts by activating syntaxin-3. In another embodiment, a combination of these mechanisms is employed.

In another embodiment, as demonstrated by the data presented herein, administration of DHA and/or UMP is efficacious in treating and/or preventing a disorder characterized by impaired synapse formation or myelination. Each possibility represents a separate embodiment of the present invention.

As provided herein, administration of PUFA and/or uridine to gerbils, whose pyrimidine metabolism resembles that of humans, increases levels of the neurite neurofibrillar proteins NF-70 and NF-M, the postsynaptic density protein PSD-95 and the vesicular protein Synapsin-1 (Example 7). Thus, administration of PUFA increases levels of synaptic membranes in brain and neural cells. In another embodiment, under the conditions utilized herein, methods of compositions of the present invention also have utility in increasing neuronal signaling. In another embodiment, under the conditions utilized herein, methods of compositions of the present invention also have utility in enhancing neural function. In another embodiment, under the conditions utilized herein, methods of compositions of the present invention also have utility in increasing neurite outgrowth. Each possibility represents a separate embodiment of the present invention.

The omega-3 fatty acid utilized in methods and compositions of the present invention is, in another embodiment, an omega-3 polyunsaturated fatty acid (PUFA). In another embodiment, the omega-3 fatty acid is DHA (Examples 1-2). DHA is an omega-3, polyunsaturated, 22-carbon fatty acid also referred to as 4,7,10,13,16,19-docosahexaenoic acid.

In another embodiment, the omega-3 fatty acid is α-linolenic acid (9,12,15-octadecatrienoic acid). In another embodiment, the omega-3 fatty acid is stearidonic acid (6,9,12,15-octadecatetraenoic acid). In another embodiment, the omega-3 fatty acid is eicosatrienoic acid (ETA; 11,14,17-eicosatrienoic acid). In another embodiment, the omega-3 fatty acid is eicsoatetraenoic acid (8,11,14,17-eicosatetraenoic acid). In another embodiment, the omega-3 fatty acid is eicosapentaenoic acid (EPA; 5,8,11,14,17-eicosapentaenoic acid). In another embodiment, the omega-3 fatty acid is eicosahexaenoic acid (also referred to as "EPA"; 5,7,9,11,14,17-eicosahexaenoic acid). In another embodiment, the omega-3 fatty acid is docosapentaenoic acid (DPA; 7,10,13,16,19-docosapenatenoic acid). In another embodiment, the omega-3 fatty acid is tetracosahexaenoic acid (6,9,12,15,18,21-tetracosahexaenoic acid). In another embodiment, the omega-3 fatty acid is any other omega-3 fatty acid known in the art. Each omega-3 fatty acid represents a separate embodiment of the present invention.

In another embodiment, the omega-3 fatty acid is an anti-inflammatory PUFA. In another embodiment, the anti-inflammatory PUFA is eicosapentaenoic acid (EPA; 5,8,11,14,17-eicosapentaenoic acid). In another embodiment, the anti-inflammatory PUFA is DHA. In another embodiment, the anti-inflammatory PUFA is any other anti-inflammatory PUFA known in the art. Each possibility represents a separate embodiment of the present invention.

As provided herein, DHA, EPA, and AA all increase brain phospholipid levels (Example 8). Thus, the effects described herein are not specific to a particular PUFA, but rather are, under the conditions utilized herein, generalizable to omega-3 and omega-6 PUFA as a family.

In another embodiment, the omega-3 fatty acid is a metabolic precursor of DHA. In another embodiment, the metabolic precursor is EPA). In another embodiment, the metabolic precursor is docosapentaenoic acid (DPA; 7,10, 13,16,19-docosapenatenoic acid). Each possibility represents a separate embodiment of the present invention.

In another embodiment, "metabolic precursor" refers to a compound that increases the concentration of the fatty acid in the bloodstream or tissues. In another embodiment, "metabolic precursor" refers to a compound that is metabolized by a tissue or enzyme of the subject to the fatty acid. In another embodiment, "metabolic precursor" refers to a compound that is metabolized by the target cell to the fatty acid. Each possibility represents a separate embodiment of the present invention.

In another embodiment of methods and compositions of the present invention, the metabolic precursor of an omega-3 fatty acid is an alpha-linolenic acid, which serves as a precursor to EPA (eicosapentaenoic acid) and DHA (docosahexaenoic acid). In another embodiment, the metabolic precursor is any other omega-3 fatty acid precursor known in the art. Each omega-3 fatty acid precursor represents a separate embodiment of the present invention.

"PUFA" refers, in another embodiment, to omega-3 fatty acid. In another embodiment, the term refers to an omega-6 fatty acid. In another embodiment, the term refers to a fatty acid with 2 or more double bonds. In another embodiment, the term refers to a fatty acid with 2 double bonds. In another embodiment, the term refers to a fatty acid with 3 double bonds. In another embodiment, the term refers to a fatty acid with more than 3 double bonds. Each possibility represents a separate embodiment of the present invention.

In another embodiment, the present invention provides a method of increasing an amount of a synaptic membrane of a neural cell or brain cell of a subject, comprising administering to the subject an omega-6 fatty acid or a metabolic precursor thereof, thereby increasing an amount of a synaptic membrane of a neural cell or brain cell of a subject. In another embodiment, the subject has a memory disorder. In another embodiment, the disorder is age-related. Each possibility represents a separate embodiment of the present invention.

In another embodiment, the present invention provides a method of increasing a level of a phospholipid of a neural cell of a subject, comprising administering to the subject an omega-6 fatty acid or a metabolic precursor thereof, thereby increasing a level of a phospholipid of a neural cell of a subject. In another embodiment, the subject has a memory disorder. In another embodiment, the disorder is age-related. Each possibility represents a separate embodiment of the present invention.

In another embodiment, the present invention provides a method of increasing a level of a phospholipid of a brain cell of a subject, comprising administering to the subject an omega-6 fatty acid or a metabolic precursor thereof, thereby increasing a level of a phospholipid of a brain cell of a subject. In another embodiment, the subject has a memory disorder. In another embodiment, the disorder is age-related. Each possibility represents a separate embodiment of the present invention.

In another embodiment, the present invention provides a method of increasing or enhancing a synthesis of a phospholipid by a neural cell or brain cell of a subject, comprising administering to the subject an omega-6 fatty acid or a metabolic precursor thereof, thereby increasing or enhancing a synthesis of a phospholipid by a neural cell or brain cell of a subject. In another embodiment, the subject has a memory disorder. In another embodiment, the disorder is age-related. Each possibility represents a separate embodiment of the present invention.

As provided herein, the results presented in Example 3 demonstrate that administration of arachidonic acid, an omega-6 fatty acid, to neural and brain cells increases their phospholipid synthesis, as evidenced by increased incorporation of labeled choline thereafter. SHSY-5Y cells are derived from a human neuroblastoma, and are used as a model system for neuronal functions. Increasing synthesis of the phospholipids results, in another embodiment, in an increase in their levels.

In another embodiment, the omega-6 fatty acid is an omega-6 polyunsaturated fatty acid (PUFA). In another embodiment, the omega-6 fatty acid is arachidonic acid (Example 3). Arachidonic acid is an omega-6,20-carbon fatty acid that is also referred to as 5,8,11,14-eicosatetraenoic acid. In another embodiment, the omega-6 fatty acid is a metabolic precursor of arachidonic acid. Each possibility represents a separate embodiment of the present invention.

In another embodiment, the omega-6 fatty acid is linoleic acid (9,12-octadecadienoic acid). In another embodiment, the omega-6 fatty acid is conjugated linoleic acid (CLA). In another embodiment, the omega-6 fatty acid is γ-linolenic acid (6,9,12-octadecatrienoic acid). In another embodiment, the omega-6 fatty acid is eicosadienoic acid (11,14-eicosadienoic acid). In another embodiment, the omega-6 fatty acid is homo-γ-linolenic acid (8,11,14-eicosatrienoic acid). In another embodiment, the omega-6 fatty acid is docosadienoic acid (13,16-docosadienoic acid). In another embodiment, the omega-6 fatty acid is docosatetraenoic acid (7,10,13,16-docosatetraenoic acid). In another embodiment, the omega-6 fatty acid is 4,7,10,13,16-docosapentaenoic acid. In another embodiment, the omega-6 fatty acid is dihomogamma linolenic acid (DGLA). In another embodiment, the omega-6 fatty acid is any other omega-6 fatty acid known in the art. Each omega-6 fatty acid represents a separate embodiment of the present invention.

In another embodiment of methods and compositions of the present invention, the metabolic precursor of an omega-6 fatty acid is linoleic acid. In another embodiment, the metabolic precursor is trans-vaccenic acid (TVA), a source of linoleic acid. In another embodiment, the metabolic precursor is any other omega-6 fatty acid precursor known in the art. Each omega-6 fatty acid precursor represents a separate embodiment of the present invention.

In another embodiment, the present invention provides a method of increasing a level of a phospholipid of a neural cell of a subject, comprising administering to the subject a composition comprising: (a) a uridine, an acyl derivative thereof, a uridine phosphate, or a CDP-choline; and (b) an omega-3 fatty acid or a metabolic precursor thereof, thereby increasing a level of a phospholipid of a neural cell of a subject. In another embodiment, the subject has a memory disorder. In another embodiment, the disorder is age-related. Each possibility represents a separate embodiment of the present invention.

As provided herein, omega-3 fatty acids and omega-6 fatty acids each act synergistically with uridine (e.g. UMP) to increase phospholipid synthesis and phospholipid levels. In another embodiment, the uridine phosphate is a uridine monophosphate (UMP).

In another embodiment, the present invention provides a method of increasing a level of a phospholipid of a brain cell of a subject, comprising administering to the subject a composition comprising: (a) a uridine, an acyl derivative thereof, a uridine phosphate, or a CDP-choline; and (b) an omega-3 fatty acid or a metabolic precursor thereof, thereby increasing a level of a phospholipid of a brain cell of a subject. In another embodiment, the subject has a memory disorder. In another embodiment, the disorder is age-related. Each possibility represents a separate embodiment of the present invention.

In another embodiment, the present invention provides a method of increasing a level of a phospholipid of a neural cell of a subject, comprising administering to the subject a composition comprising: (a) a uridine, an acyl derivative thereof, a uridine phosphate, or a CDP-choline; and (b) an omega-6 fatty acid or a metabolic precursor thereof, thereby increasing a level of a phospholipid of a neural cell of a subject. In another embodiment, the subject has a memory disorder. In another embodiment, the disorder is age-related. Each possibility represents a separate embodiment of the present invention.

In another embodiment, the present invention provides a method of increasing a level of a phospholipid of a brain cell of a subject, comprising administering to the subject a composition comprising: (a) a uridine, an acyl derivative thereof, a uridine phosphate, or a CDP-choline; and (b) an omega-6 fatty acid or a metabolic precursor thereof, thereby increasing a level of a phospholipid of a brain cell of a subject. In another embodiment, the subject has a memory disorder. In another embodiment, the disorder is age-related. Each possibility represents a separate embodiment of the present invention.

In another embodiment, the present invention provides a method of increasing or enhancing a synthesis of a phospholipid by a neural cell or brain cell of a subject, comprising administering to the subject a composition comprising: (a) a uridine, an acyl derivative thereof, a uridine phosphate, or a CDP-choline; and (b) an omega-3 fatty acid or a metabolic precursor thereof, thereby increasing or enhancing a synthesis of a phospholipid by a neural cell or brain cell of a subject. In another embodiment, the subject has a memory disorder. In another embodiment, the disorder is age-related. Each possibility represents a separate embodiment of the present invention.

In another embodiment, the present invention provides a method of increasing or enhancing a synthesis of a phospholipid by a neural cell or brain cell of a subject, comprising administering to the subject a composition comprising: (a) a uridine, an acyl derivative thereof, a uridine phosphate, or a CDP-choline; and (b) an omega-6 fatty acid or a metabolic precursor thereof, thereby increasing or enhancing a synthesis of a phospholipid by a neural cell or brain cell of a subject. In another embodiment, the subject has a memory disorder. In another embodiment, the disorder is age-related. Each possibility represents a separate embodiment of the present invention.

In another embodiment, the present invention provides a method of increasing an amount of a synaptic membrane of a neural cell or brain cell of a subject, comprising administering to the subject a composition comprising: (a) a uridine, an acyl derivative thereof, a uridine phosphate, or a CDP-choline; and (b) an omega-3 fatty acid or a metabolic precursor thereof, thereby increasing an amount of a synaptic membrane of a neural cell or brain cell of a subject. In another embodiment, the subject has a memory disorder. In another embodiment, the disorder is age-related. Each possibility represents a separate embodiment of the present invention.

In another embodiment, the present invention provides a method of increasing an amount of a synaptic membrane of a neural cell or brain cell of a subject, comprising administering to the subject a composition comprising: (a) a uridine, an acyl derivative thereof, a uridine phosphate, or a CDP-choline; and (b) an omega-6 fatty acid or a metabolic precursor thereof, thereby increasing an amount of a synaptic membrane of a neural cell or brain cell of a subject. In another embodiment, the subject has a memory disorder. In another embodiment, the disorder is age-related. Each possibility represents a separate embodiment of the present invention.

Methods for measuring the amount of synaptic membrane in a subject's brain are well known in the art, and are described, for example, in Oertner T G et al (Facilitation at single synapses probed with optical quantal analysis. Nat. Neurosci. 2002 July; 5(7):657-64); Bloodgood B L et al (Neuronal activity regulates diffusion across the neck of dendritic spines. Science. 2005 Nov. 4; 310(5749):866-9); El Fakhri G et al (Generalized five-dimensional dynamic and spectral factor analysis. Med. Phys. 2006 April; 33(4): 1016-24); and Pautler R G. Biological applications of manganese-enhanced magnetic resonance imaging. Methods Mol. Med. 2006; 124:365-86). Each method represents a separate embodiment of the present invention.

In another embodiment, the present invention provides a method of treating a subject with Alzheimer's disease, comprising administering to the subject an omega-3 fatty acid or a metabolic precursor thereof, whereby the omega-3 fatty acid or metabolic precursor thereof increases a synthesis of a phospholipid by the neural cell or brain cell, thereby treating a subject with Alzheimer's disease.

In another embodiment, the present invention provides a method of treating a subject with Alzheimer's disease, comprising administering to the subject an omega-6 fatty acid or a metabolic precursor thereof, whereby the omega-6 fatty acid or metabolic precursor thereof increases a synthesis of a phospholipid by the neural cell or brain cell, thereby treating a subject with Alzheimer's disease.

In another embodiment, the present invention provides a method of treating a subject with Alzheimer's disease, comprising contacting a neural cell of the subject with a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by the neural cell or brain cell, thereby treating a subject with Alzheimer's disease.

In another embodiment, the present invention provides a method of treating a subject with Alzheimer's disease, comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by the neural cell or brain cell, thereby treating a subject with Alzheimer's disease.

As provided herein, compositions comprising omega-3 fatty acids, omega-6 fatty acids, and/or uridine increase the amount of synaptic membranes in neural cells. Thus, compositions of the present invention have utility in treating Alzheimer's disease.

In another embodiment of methods and compositions of the present invention, stimulation of phospholipid synthesis increases phospholipid levels in the target brain or neural cell. Sufficient phospholipid levels are important, in another embodiment, in many aspects of neural function, e.g. synaptic signaling, neurotransmitter function, neurite branching and outgrowth etc, and are also important, in another embodiment, in proper brain function.

In another embodiment, the Alzheimer's disease is at an early stage. In another embodiment, the Alzheimer's disease is at a mild stage. In another embodiment, the Alzheimer's disease is at a moderate stage. In another embodiment, the Alzheimer's disease is at a late stage. In another embodiment, the Alzheimer's disease is at a severe stage. In another embodiment, the Alzheimer's disease is at an undetermined stage. In another embodiment, the Alzheimer's disease is at any stage of the disease known in the art. Each stage represents a separate embodiment of the present invention.

In another embodiment, the stage of Alzheimer's disease is assessed using the Functional Assessment Staging (FAST) scale. The FAST scale was developed by Dr Reisberg and colleagues. It divides the progression of Alzheimer's disease into 16 successive stages under 7 major headings of functional abilities and losses. The major headings are as follows: Stage 1 is defined as a normal adult with no decline in function or memory. Stage 2 is defined as a normal older adult who has some personal awareness of functional decline, typically complaining of memory deficit and forgetting the names of familiar people and places. Stage 3 (early Alzheimer's disease) becomes manifest in demanding job situations. Signs include one or more of the following; disorientation when traveling to an unfamiliar location; reports by colleagues of decreased performance; name- and word-finding deficits; reduced ability to recall information from a passage in a book or to remember a name of a person newly introduced to them; misplacing of valuable objects; decreased concentration. In stage 4 (mild Alzheimer's Disease), the patient may require assistance in complicated tasks such as planning a party or handling finances, exhibits problems remembering life events, and has difficulty concentrating and traveling. In stage 5 (moderate Alzheimer's disease, the patient requires assistance to perform everyday tasks such as choosing proper attire. Disorientation in time, and inability to recall important information of their current lives, occur, but patient can still remember major information about themselves, their family and others. In stage 6

(moderately severe Alzheimer's disease, the patient begins to forget significant amounts of information about themselves and their surroundings and require assistance dressing, bathing, and toileting. Urinary incontinence and disturbed patterns of sleep occur. Personality and emotional changes become quite apparent. Because patients cannot remember information long enough to act on their thoughts, they lose willpower (cognitive abulla). In stage 7 (severe Alzheimer's disease), speech ability becomes limited to just six or seven words and intelligible vocabulary may be limited to a single word. The patient loses the ability to walk, sit up, smile and eventually cannot hold up the head. Each stage of Alzheimer's disease represents a separate embodiment of the present invention.

In another embodiment, the present invention provides a method of raising a brain PC level in a subject, comprising administering to the subject a composition of the present invention, whereby the composition increases a synthesis of a phospholipid by a neural cell or brain cell of the subject, thereby raising a brain PC level in a subject. In another embodiment, the subject has a memory disorder. In another embodiment, the disorder is age-related. Each possibility represents a separate embodiment of the present invention.

In another embodiment, the present invention provides a method of raising a brain SM level in a subject, comprising administering to the subject a composition of the present invention, whereby the composition increases a synthesis of a phospholipid by a neural cell or brain cell of the subject, thereby raising a brain SM level in a subject. In another embodiment, the subject has a memory disorder. In another embodiment, the disorder is age-related. Each possibility represents a separate embodiment of the present invention.

In another embodiment, the present invention provides a method of raising a brain PI level in a subject, comprising administering to the subject a composition of the present invention, whereby the composition increases a synthesis of a phospholipid by a neural cell or brain cell of the subject, thereby raising a brain PI level in a subject. In another embodiment, the subject has a memory disorder. In another embodiment, the disorder is age-related. Each possibility represents a separate embodiment of the present invention.

In another embodiment, the present invention provides a method of raising a brain PE level in a subject, comprising administering to the subject a composition of the present invention, whereby the composition increases a synthesis of a phospholipid by a neural cell or brain cell of the subject, thereby raising a brain PE level in a subject. In another embodiment, the subject has a memory disorder. In another embodiment, the disorder is age-related. Each possibility represents a separate embodiment of the present invention.

In another embodiment, the present invention provides a method of raising a brain PS level in a subject, comprising administering to the subject a composition of the present invention, whereby the composition increases a synthesis of a phospholipid by a neural cell or brain cell of the subject, thereby raising a brain PS level in a subject. In another embodiment, the subject has a memory disorder. In another embodiment, the disorder is age-related. Each possibility represents a separate embodiment of the present invention.

In another embodiment, the present invention provides a method of improving a cognitive function in a subject, comprising administering to the subject a composition of the present invention, whereby the composition increases a synthesis of a phospholipid by a neural cell or brain cell of the subject, thereby improving a cognitive function in a subject. In another embodiment, the subject has a memory disorder. In another embodiment, the disorder is age-related. Each possibility represents a separate embodiment of the present invention.

As provided herein, DHA and UMP improved the performance of animals on a memory test (Example 10). Thus, methods and compositions of the present invention are efficacious in improving and enhancing memory and other cognitive functions.

As provided herein, administration of PUFA and/or uridine increases brain phospholipid levels and synthesis, levels of neurite neurofibrillar proteins, and amount of synaptic membranes. Thus, compositions and methods of the present invention increase and enhance cognitive function, neurological function, intelligence, synaptic transmission, and neurotransmitter levels and activity.

In another embodiment, the present invention provides a method of improving a neurological function in a subject, comprising administering to the subject a composition of the present invention, whereby the composition increases a synthesis of a phospholipid by a neural cell or brain cell of the subject, thereby improving a neurological function in a subject. In another embodiment, the subject has a memory disorder. In another embodiment, the disorder is age-related. Each possibility represents a separate embodiment of the present invention.

In another embodiment, the neurological function that is improved by a method of the present invention is a synaptic transmission. In another embodiment, the synaptic transmission is adjacent to a motor neuron. In another embodiment, the synaptic transmission is adjacent to an interneuron. In another embodiment, the synaptic transmission is adjacent to a sensory neuron. Each type of synaptic transmission represents a separate embodiment of the present invention.

In another embodiment, the neurological function that is improved or enhanced is a function of a neurotransmitter. In one embodiment, improving or enhancing a function of a neurotransmitter occurs by means of increasing a level of the neurotransmitter in a synapse. In another embodiment, improving or enhancing a function of a neurotransmitter occurs by means of increasing the release of the neurotransmitter into a synapse. In another embodiment, improving or enhancing a function of a neurotransmitter occurs without changing the level or release of the neurotransmitter in a synapse. Each possibility represents a separate embodiment of the present invention.

In another embodiment, "improving" a cognitive or neurological function or intelligence refers to effecting a 10% improvement thereof. In another embodiment, the term refers to effecting a 20% improvement thereof. In another embodiment, the term refers to effecting a 30% improvement thereof. In another embodiment, the term refers to effecting a 40% improvement thereof. In another embodiment, the term refers to effecting a 50% improvement thereof. In another embodiment, the term refers to effecting a 60% improvement thereof. In another embodiment, the term refers to effecting a 70% improvement thereof. In another embodiment, the term refers to effecting an 80% improvement thereof. In another embodiment, the term refers to effecting a 90% improvement thereof. In another embodiment, the term refers to effecting a 100% improvement thereof. Each possibility represents a separate embodiment of the present invention.

In another embodiment, improvement of a cognitive or neurological function or intelligence is assessed relative to the function before beginning treatment. In another embodiment, the improvement is assessed relative to an untreated subject. In another embodiment, the improvement is assessed according to a standardized criterion such as, for example, a test or the like. Each type of improvement of cognitive activity represents a separate embodiment of the present invention.

In another embodiment, improvement of a cognitive or neurological function or intelligence is assessed by the number of connections between neurons in the subject's brain. In another embodiment, the improvement is assessed by the number of capillaries in the subject's brain, or in a specific region of the subject's brain. In another embodiment, the improvement is assessed by neural activity. In another embodiment, the improvement is assessed by neural function. In another embodiment, the improvement is assessed by linguistic function. In another embodiment, the improvement is assessed by ability to communicate. In another embodiment, the improvement is assessed by measurement of levels of acetylcholine or other neurotransmitters or brain chemicals correlated with cognitive function. In another embodiment, the improvement is assessed by Positron Emission Tomography (PET) scanning of the subject's brain. In another embodiment, the improvement is assessed by magnetic resonance imaging (MRI) scanning of the subject's brain. In another embodiment, the improvement is assessed by Cognitive Abilities Screening Instrument (CASI) (Peila R et al, Stroke. 32: 2882-9, 2001). In another embodiment, the improvement is assessed by a test such as, for example, the tests disclosed herein (Example 13). In another embodiment, the Mini-Mental test (Tsai L et al, The Mini-Mental State Test and computerized tomography. Am J Psychiatry. 1979 April; 136(4A):436-8) is utilized. Additional methods for assessing improvement of cognitive function are well known in the art, and are described, for example in Antonova E et al (Schizophr Res. 2004 Oct. 1; 70(2-3):117-45) and in Cognitive Function Analysis (Greenwood Pub Group, 1998). Each method represents a separate embodiment of the present invention.

In another embodiment, the present invention provides a method of inhibiting a decline in synapse numbers in a brain of a subject, comprising administering to the subject a composition of the present invention, whereby the composition increases a synthesis of a phospholipid by a neural cell or brain cell of the subject, thereby inhibiting a decline in synapse numbers in a brain of a subject. In another embodiment, the subject has a memory disorder. In another embodiment, the disorder is age-related. Each possibility represents a separate embodiment of the present invention.

In another embodiment, the present invention provides a method of increasing an amount or level of a neurotransmitter in the brain or CNS of a subject, the method comprising administering to the subject an omega-3 fatty acid or a metabolic precursor thereof, whereby the omega-3 fatty acid or metabolic precursor thereof increases a synthesis of a phospholipid in the brain or CNS, thereby increasing an amount or level of a neurotransmitter in the brain or CNS of a subject. In another embodiment, the subject has a memory disorder. In another embodiment, the disorder is age-related. Each possibility represents a separate embodiment of the present invention.

In another embodiment, the present invention provides a method of increasing an amount or level of a neurotransmitter in the brain or CNS of a subject, the method comprising administering to the subject an omega-6 fatty acid or a metabolic precursor thereof, whereby the omega-6 fatty acid or metabolic precursor thereof increases a synthesis of a phospholipid in the brain or CNS, thereby increasing an amount or level of a neurotransmitter in the brain or CNS of a subject. In another embodiment, the subject has a memory disorder. In another embodiment, the disorder is age-related. Each possibility represents a separate embodiment of the present invention.

In another embodiment, the present invention provides a method of increasing an amount or level of a neurotransmitter in the brain or CNS of a subject, the method comprising administering to the subject a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid in the brain or CNS, thereby increasing an amount or level of a neurotransmitter in the brain or CNS of a subject. In another embodiment, the subject has a memory disorder. In another embodiment, the disorder is age-related. Each possibility represents a separate embodiment of the present invention.

In another embodiment, the present invention provides a method of increasing an amount or level of a neurotransmitter in the brain or CNS of a subject, the method comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid in the brain or CNS, thereby increasing an amount or level of a neurotransmitter in the brain or CNS of a subject. In another embodiment, the subject has a memory disorder. In another embodiment, the disorder is age-related. Each possibility represents a separate embodiment of the present invention.

In one embodiment, the neurotransmitter whose levels or activity, or release is affected by methods of the present invention is acetylcholine. In another embodiment, the neurotransmitter is glutamate. In another embodiment, the neurotransmitter is dopamine. In another embodiment, the neurotransmitter is serotonin. In another embodiment, the neurotransmitter is 5-hydroxytryptamine (5-HT). In another embodiment, the neurotransmitter is GABA. In another embodiment, the neurotransmitter is any other neurotransmitter known in the art. Each type of neurotransmitter represents a separate embodiment of the present invention.

In another embodiment, the present invention provides a method of increasing or enhancing an ability of a brain cell of a subject to repeatedly release an effective quantity of a neurotransmitter into a synapse, the method comprising administering to the subject an omega-3 fatty acid or a metabolic precursor thereof, whereby the omega-3 fatty acid or metabolic precursor thereof increases a synthesis of a phospholipid by the brain cell, thereby increasing or enhancing an ability of a brain cell of a subject to repeatedly release an effective quantity of a neurotransmitter into a synapse. In another embodiment, the subject has a memory disorder. In another embodiment, the disorder is age-related. Each possibility represents a separate embodiment of the present invention.

As provided herein, dendritic spine density increased in animals administered DHA and/or uridine (Example 9). Thus, compositions of the present invention increase the number and size of synapses in the brain and the ability of brain cells to signal via neurotransmitters.

In another embodiment, the present invention provides a method of increasing or enhancing an ability of a brain cell of a subject to repeatedly release an effective quantity of a neurotransmitter into a synapse, the method comprising administering to the subject an omega-6 fatty acid or a metabolic precursor thereof, whereby the omega-6 fatty acid or metabolic precursor thereof increases a synthesis of a phospholipid by the brain cell, thereby increasing or enhancing an ability of a brain cell of a subject to repeatedly release an effective quantity of a neurotransmitter into a synapse. In another embodiment, the subject has a memory disorder. In another embodiment, the disorder is age-related. Each possibility represents a separate embodiment of the present invention.

In another embodiment, the present invention provides a method of increasing or enhancing an ability of a brain cell of a subject to repeatedly release an effective quantity of a neurotransmitter into a synapse, the method comprising administering to the subject a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by the brain cell, thereby increasing or enhancing an ability of a brain cell of a subject to repeatedly release an effective quantity of a neurotransmitter into a synapse. In another embodiment, the subject has a memory disorder. In another embodiment, the disorder is age-related. Each possibility represents a separate embodiment of the present invention.

In another embodiment, the present invention provides a method of increasing or enhancing an ability of a brain cell of a subject to repeatedly release an effective quantity of a neurotransmitter into a synapse, the method comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by the brain cell, thereby increasing or enhancing an ability of a brain cell of a subject to repeatedly release an effective quantity of a neurotransmitter into a synapse. In another embodiment, the subject has a memory disorder. In another embodiment, the disorder is age-related. Each possibility represents a separate embodiment of the present invention.

As provided herein, administration of PUFA and/or uridine increases brain phospholipid levels and synthesis, levels of neurite neurofibrillar proteins, and amount of synaptic membranes. Thus, compositions and methods of the present invention increase and enhance neurotransmitter release and amounts.

In another embodiment, the present invention provides a method of improving or enhancing an intelligence of a subject, comprising administering to the subject a composition of the present invention, whereby the composition increases a synthesis of a phospholipid by a neural cell or brain cell of the subject, thereby improving or enhancing an intelligence of a subject. In another embodiment, the subject has a memory disorder. In another embodiment, the disorder is age-related. Each possibility represents a separate embodiment of the present invention.

In another embodiment, the present invention provides a method of increasing the number of dendritic spines in the brain or a region thereof of a subject, comprising administering to the subject a composition of the present invention, whereby the composition increases a synthesis of a phospholipid by a neural cell or brain cell of the subject, thereby increasing the number of dendritic spines in the brain or a region thereof of a subject. In another embodiment, the subject has a memory disorder. In another embodiment, the disorder is age-related. Each possibility represents a separate embodiment of the present invention.

The intelligence that is improved or enhanced by methods and compositions of the present invention is, in another embodiment, linguistic intelligence. In another embodiment, the intelligence is musical intelligence. In another embodiment, the intelligence is spatial intelligence. In another embodiment, the intelligence is bodily intelligence. In another embodiment, the intelligence is interpersonal intelligence. In another embodiment, the intelligence is interpersonal intelligence. In another embodiment, the intelligence is interpersonal intelligence. In another embodiment, the intelligence is logico-mathematical intelligence. In another embodiment, the intelligence is any other type of intelligence known in the art. Each type of intelligence represents a separate embodiment of the present invention.

In another embodiment, the present invention provides a method of facilitating or enhancing brain repair, comprising administering to the subject an omega-3 fatty acid or a metabolic precursor thereof, thereby facilitating or enhancing brain repair. In another embodiment, the subject has a memory disorder. In another embodiment, the disorder is age-related. Each possibility represents a separate embodiment of the present invention.

In another embodiment, the present invention provides a method of facilitating or enhancing brain repair, comprising administering to the subject an omega-6 fatty acid or a metabolic precursor thereof, thereby facilitating or enhancing brain repair. In another embodiment, the subject has a memory disorder. In another embodiment, the disorder is age-related. Each possibility represents a separate embodiment of the present invention.

In another embodiment, the present invention provides a method of facilitating or enhancing brain repair, comprising administering to the subject a composition comprising: (a) a uridine, an acyl derivative thereof, a uridine phosphate, or a CDP-choline; and (b) an omega-3 fatty acid or a metabolic precursor thereof, thereby facilitating or enhancing brain repair. In another embodiment, the subject has a memory disorder. In another embodiment, the disorder is age-related. Each possibility represents a separate embodiment of the present invention.

In another embodiment, the present invention provides a method of facilitating or enhancing brain repair, comprising administering to the subject a composition comprising: (a) a uridine, an acyl derivative thereof, a uridine phosphate, or a CDP-choline; and (b) an omega-6 fatty acid or a metabolic precursor thereof, thereby facilitating or enhancing brain repair. In another embodiment, the subject has a memory disorder. In another embodiment, the disorder is age-related. Each possibility represents a separate embodiment of the present invention.

In another embodiment, the brain repair is facilitated or enhanced following a stroke. In another embodiment, the brain repair is facilitated or enhanced following a brain injury. In another embodiment, the brain repair is facilitated or enhanced following any other event, disease or disorder known in the art that necessitates brain repair. Each possibility represents another embodiment of the present invention.

In another embodiment, the subject whose cognitive function, neurological function, intelligence, synaptic transmission, or neurotransmitter levels and activity is enhanced or improved by a composition or method of the present invention has a cognitive impairment or memory disorder. In another embodiment, the subject is aged. In another embodiment, the subject has no cognitive impairment or memory disorder. Each possibility represents a separate embodiment of the present invention.

In another embodiment, the present invention provides a method of increasing a sensitivity of a neuron to a stimulus, comprising contacting the neuron with a composition of the present invention, thereby increasing a sensitivity of a neuron to a stimulus. In another embodiment, the subject has a memory disorder. In another embodiment, the disorder is age-related. Each possibility represents a separate embodiment of the present invention.

As provided herein, administration of PUFA and/or uridine increases brain phospholipid levels and synthesis, levels of neurite neurofibrillar proteins, and amount of synaptic membranes. Thus, compositions and methods of the present invention increase and enhance the sensitivity of neurons to stimuli and the size and number of synapses in the brain and central nervous system (CNS).

In another embodiment, the present invention provides a method of increasing an average synapse size in a brain of a subject, comprising administering to the subject a composition of the present invention, thereby increasing an average synapse size in a brain of a subject. In another embodiment, the subject has a memory disorder. In another embodiment, the disorder is age-related. Each possibility represents a separate embodiment of the present invention.

In another embodiment, the present invention provides a method of increasing the number of synapses in a brain of a subject, comprising administering to the subject an omega-3 fatty acid or a metabolic precursor thereof, thereby increasing the number of synapses in a brain of a subject. In another embodiment, the subject has a memory disorder. In another embodiment, the disorder is age-related. Each possibility represents a separate embodiment of the present invention.

In another embodiment, the present invention provides a method of increasing the number of synapses in a brain of a subject, comprising administering to the subject an omega-6 fatty acid or a metabolic precursor thereof, thereby increasing the number of synapses in a brain of a subject. In another embodiment, the subject has a memory disorder. In another embodiment, the disorder is age-related. Each possibility represents a separate embodiment of the present invention.

In another embodiment, the present invention provides a method of increasing the number of synapses in a brain of a subject, comprising administering to the subject a composition comprising: (a) a uridine, an acyl derivative thereof, a uridine phosphate, or a CDP-choline; and (b) an omega-3 fatty acid or a metabolic precursor thereof, thereby increasing the number of synapses in a brain of a subject. In another embodiment, the subject has a memory disorder. In another embodiment, the disorder is age-related. Each possibility represents a separate embodiment of the present invention.

In another embodiment, the present invention provides a method of increasing the number of synapses in a brain of a subject, comprising administering to the subject a composition comprising: (a) a uridine, an acyl derivative thereof, a uridine phosphate, or a CDP-choline; and (b) an omega-6 fatty acid or a metabolic precursor thereof, thereby increasing the number of synapses in a brain of a subject. In another embodiment, the subject has a memory disorder. In another embodiment, the disorder is age-related. Each possibility represents a separate embodiment of the present invention.

Methods for measuring and estimating the average synapse size, number of synapses, and level of synaptic activity and neurotransmitter release in the brain and CNS of a subject are well known in the art, and are disclosed, for example, in Wheeler D W et al (Estimating use-dependent synaptic gain in autonomic ganglia by computational simulation and dynamic-clamp analysis. J Neurophysiol. 2004 November; 92(5):2659-71), Viele K et al (Estimating the number of release sites and probability of firing within the nerve terminal by statistical analysis of synaptic charge. Synapse. 2003 January; 47(1):15-25), and DeFelipe J et al (Estimation of the number of synapses in the cerebral cortex: methodological considerations. Cereb Cortex. 1999 October-November; 9(7):722-32). Each possibility represents a separate embodiment of the present invention.

In another embodiment, the present invention provides a method of stimulating or enhancing a production of a membrane of a brain cell or a neural cell of a subject, comprising administering to the subject an omega-3 fatty acid or a metabolic precursor thereof, thereby stimulating or enhancing a production of a membrane of a brain cell or a neural cell of a subject. In another embodiment, the subject has a memory disorder. In another embodiment, the disorder is age-related. Each possibility represents a separate embodiment of the present invention.

In another embodiment, the present invention provides a method of stimulating or enhancing a production of a membrane of a brain cell or a neural cell of a subject, comprising administering to the subject an omega-6 fatty acid or a metabolic precursor thereof, thereby stimulating or enhancing a production of a membrane of a brain cell or a neural cell of a subject. In another embodiment, the subject has a memory disorder. In another embodiment, the disorder is age-related. Each possibility represents a separate embodiment of the present invention.

In another embodiment, the present invention provides a method of stimulating or enhancing a production of a membrane of a brain cell or a neural cell of a subject, comprising administering to the subject a composition comprising: (a) a uridine, an acyl derivative thereof, a uridine phosphate, or a CDP-choline; and (b) an omega-3 fatty acid or a metabolic precursor thereof, thereby stimulating or enhancing a production of a membrane of a brain cell or a neural cell of a subject. In another embodiment, the subject has a memory disorder. In another embodiment, the disorder is age-related. Each possibility represents a separate embodiment of the present invention.

In another embodiment, the present invention provides a method of stimulating or enhancing a production of a membrane of a brain cell or a neural cell of a subject, comprising administering to the subject a composition comprising: (a) a uridine, an acyl derivative thereof, a uridine phosphate, or a CDP-choline; and (b) an omega-6 fatty acid or a metabolic precursor thereof, thereby stimulating or enhancing a production of a membrane of a brain cell or a neural cell of a subject. In another embodiment, the subject has a memory disorder. In another embodiment, the disorder is age-related. Each possibility represents a separate embodiment of the present invention.

In another embodiment, methods of the present invention increase phospholipid levels while substantially preserving the ratios of 2 or more phospholipids in the target brain or neural cell. In another embodiment, methods of the present invention increase phospholipid levels while substantially preserving the ratios of 3 or more phospholipids in the target brain or neural cell. In another embodiment, methods of the present invention increase phospholipid levels while substantially preserving the ratios of 4 or more phospholipids in the target brain or neural cell. In another embodiment, the phospholipids are selected from PC, PE, PS, and sphingomyelin (SM). In another embodiment, substantial preservation of these ratios is important in the above aspects of neural and brain function. Each possibility represents a separate embodiment of the present invention.

"Substantially preserving" refers, in another embodiment, to a deviation of less than 10% from the previous ratio. In another embodiment, "substantially preserving" refers to a deviation of less than 15%. In another embodiment, the deviation is less than 20%. In another embodiment, the deviation is less than 25%. In another embodiment, the deviation is less than 30%. In another embodiment, the deviation is less than 35%. In another embodiment, the deviation is less than 40%. In another embodiment, the deviation is less than 45%. In another embodiment, the deviation is less than 50%. In another embodiment, the deviation is less than 55%. In another embodiment, the deviation is less than 60%. In another embodiment, the deviation is less than 65%. In another embodiment, the deviation is less than 70%. In another embodiment, the deviation is less than 75%. In another embodiment, the deviation is less than 80%. In another embodiment, the deviation is less than 85%. In another embodiment, the deviation is less than 90%. In another embodiment, the deviation is less than 95%. In another embodiment, the deviation is less than 90%. Each possibility represents a separate embodiment of the present invention.

In another embodiment of methods of the present invention, stimulation of phospholipid synthesis enhances neurite branching. In another embodiment, stimulation of phospholipid synthesis enhances neurite outgrowth. In another embodiment, stimulation of phospholipid synthesis increases the pool of phospholipid moieties that can be released via the activation of phospholipases. Some of the phospholipid moieties are bioactive, such as inositol 1,4,5-trisphosphate ($IP_3$), diacylglycerol (DAG), and lyso-platelet-activating factor (lyso-PAF), which upon further metabolism, gives rise to the bioactive lipid, PAF (1-0-alkyl-2-acetyl-sn-3-glycerol-3-phosphocholine).

In another embodiment, stimulation of phospholipid synthesis protects synaptic membranes against stress. In another embodiment, the stress is oxidative stress. In another embodiment, the stress is any other type of stress known in the art.

Each of these effects of stimulation of phospholipid synthesis enhances, in another embodiment, neurotransmitter-mediated signaling, thus slowing memory loss. In another embodiment, memory loss or impairment is halted due to one of the above effects. In another embodiment, memory loss is reversed due to one of the above effects. Each of the above effects of stimulation of phospholipid synthesis, and each of the above consequences thereof, represents a separate embodiment of the present invention.

In another embodiment, the present invention provides a method of treating a subject with a memory impairment or memory loss, comprising contacting a neural cell of the subject with an omega-3 fatty acid or a metabolic precursor thereof, whereby the omega-3 fatty acid or metabolic precursor thereof increases a synthesis of a phospholipid by the neural cell or brain cell, thereby treating a subject with a memory impairment or memory loss.

In another embodiment, the present invention provides a method of treating a subject with memory impairment or memory loss, comprising contacting a neural cell of the subject with an omega-6 fatty acid or a metabolic precursor thereof, whereby the omega-6 fatty acid or metabolic precursor thereof increases a synthesis of a phospholipid by the neural cell or brain cell, thereby treating a subject with a memory impairment or memory loss.

In another embodiment, the present invention provides a method of treating a subject with a memory impairment or memory loss, comprising contacting a neural cell of the subject with a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by the neural cell or brain cell, thereby treating a subject with a memory impairment or memory loss.

In another embodiment, the present invention provides a method of treating a subject with memory impairment or memory loss, comprising contacting a neural cell of the subject with a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by the neural cell or brain cell, thereby treating a subject with a memory impairment or memory loss.

In another embodiment, the memory impairment is age-related. In another embodiment, the memory impairment is secondary to a cerebrovascular disease. In another embodiment, the memory impairment is secondary to a stroke. The stroke is, in another embodiment, a clinical stroke. In another embodiment, the stroke is a subclinical stroke. In another embodiment, the memory impairment results from multiple small subclinical strokes. In another embodiment, the memory impairment is secondary to a cardiovascular cause. In another embodiment, the memory impairment is secondary to an age-related cardiovascular cause.

In another embodiment, the memory impairment is secondary to a depression, e.g. a result of the depression. As is known in the art, depressed people often exhibit memory disturbances, even to the extent that older people with depression are mistakenly diagnosed, Alzheimer's disease. Methods and compositions of the present invention will increase, in another embodiment, the release of neurotransmitters known to be involved both in depression (e.g. dopamine, norepinephrine, and serotonin) and in memory impairment (e.g. acetylcholine).

In another embodiment, the memory impairment is secondary to insomnia.

In another embodiment, the memory impairment results from any other cause of memory impairment known in the art. Each cause of memory impairment or memory loss represents a separate embodiment of the present invention.

"Age-related," in another embodiment, refers to a consequence of advanced age. In another embodiment, the age is over 65 years. In another embodiment, the age is over 60 years. In another embodiment, the age is over 55 years. In another embodiment, the age is over 68 years. In another embodiment, the age is over 70 years. In another embodiment, the age is over 72 years. In another embodiment, the age is over 75 years. In another embodiment, the age is over 78 years. In another embodiment, the age is over 80 years. In another embodiment, the age is over 85 years. In another embodiment, the age is over 90 years. In another embodiment, "age-related" refers to a consequence of any age associated with memory impairment as a result of any disease or disorder comprising memory impairment. Each possibility represents a separate embodiment of the present invention.

The subject of methods of the present invention is, in one embodiment, a human. In another embodiment, the subject is a female. In another embodiment, the subject is a male. In another embodiment, the subject is a pregnant female. In another embodiment, the subject is a nursing female. In another embodiment, the subject is a baby. In another embodiment, the subject is a child. In another embodiment, the subject is a young child. In another embodiment, the subject is an adult. In another embodiment, the subject is an aging adult. In another embodiment, "aging" refers to any of the embodiments enumerated above. Each possibility represents a separate embodiment of the present invention.

"Baby" refers, in another embodiment, to a subject under the age of 1 year. In another embodiment, the term refers to a subject under the age of 18 months. In another embodiment, the term refers to a subject under the age of 6 months. In another embodiment, the term refers to a subject under the age of 7 months. In another embodiment, the term refers to a subject under the age of 8 months. In another embodiment, the term refers to a subject under the age of 9 months. In another embodiment, the term refers to a subject under the age of 10 months. In another embodiment, the term refers to a subject under the age of 11 months. In another embodiment, the term refers to a subject under the age of 13 months. In another embodiment, the term refers to a subject under the age of 14 months. In another embodiment, the term refers to a subject under the age of 16 months. In another embodiment, the term refers to a subject under the age of 20 months. In another embodiment, the term refers to a subject under the age of 2 years. In another embodiment, the term refers to a subject that has not yet been weaned. In another embodiment, the term refers to a subject that has been weaned, but is within one of the above age ranges. Each possibility represents a separate embodiment of the present invention.

"Child" refers, in another embodiment, to a subject under the age of 18 years. In another embodiment, the term refers to a subject under the age of 17 years. In another embodiment, the term refers to a subject under the age of 16 years. In another embodiment, the term refers to a subject under the age of 15 years. In another embodiment, the term refers to a subject under the age of 14 years. In another embodiment, the term refers to a subject under the age of 13 years. In another embodiment, the term refers to a subject under the age of 12 years. In another embodiment, the term refers to a subject under the age of 11 years. In another embodiment, the term refers to a subject under the age of 10 years. In another embodiment, the term refers to a subject under the age of 9 years. In another embodiment, the term refers to a subject under the age of 8 years. In another embodiment, the term refers to a subject under the age of 7 years.

"Young child" refers, in another embodiment, to a subject under the age of 7 years. In another embodiment, the term refers to a subject under the age of 6 years. In another embodiment, the term refers to a subject under the age of 5 years. In another embodiment, the term refers to a subject under the age of 4 years. In another embodiment, the term refers to a subject under the age of 3½ years. In another embodiment, the term refers to a subject under the age of 3 years. In another embodiment, the term refers to a subject under the age of 2½ years. Each possibility represents a separate embodiment of the present invention.

"Adult" refers, in other embodiments, to a subject over one of the ages listed above as an upper limit for a child. In another embodiment, the term refers to a subject over one of the ages listed above as an upper limit for a young child. Each possibility represents a separate embodiment of the present invention.

In another embodiment, the present invention provides a method of treating a subject with Pick's disease, comprising administering to the subject an omega-3 fatty acid or a metabolic precursor thereof, whereby the omega-3 fatty acid or metabolic precursor thereof increases a synthesis of a phospholipid by a neural cell or brain cell of the subject, thereby treating a subject with Pick's disease. In another embodiment, the present invention provides a method of treating a subject with Lewy Body disease, comprising administering to the subject an omega-3 fatty acid or a metabolic precursor thereof, whereby the omega-3 fatty acid or metabolic precursor thereof increases a synthesis of a phospholipid by a neural cell or brain cell of the subject, thereby treating a subject with Lewy Body disease. In another embodiment, the present invention provides a method of treating a subject with Huntington's disease, comprising administering to the subject an omega-3 fatty acid or a metabolic precursor thereof, whereby the omega-3 fatty acid or metabolic precursor thereof increases a synthesis of a phospholipid by a neural cell or brain cell of the subject, thereby treating a subject with Huntington's disease. In another embodiment, the present invention provides a method of treating a subject with a mild cognitive impairment (MCI), comprising administering to the subject an omega-3 fatty acid or a metabolic precursor thereof, whereby the omega-3 fatty acid or metabolic precursor thereof increases a synthesis of a phospholipid by a neural cell or brain cell of the subject, thereby treating a subject with MCI. Each possibility represents a separate embodiment of the present invention.

In another embodiment, the present invention provides a method of treating a subject with Pick's disease, comprising administering to the subject an omega-6 fatty acid or a metabolic precursor thereof, whereby the omega-6 fatty acid or metabolic precursor thereof increases a synthesis of a phospholipid by a neural cell or brain cell of the subject, thereby treating a subject with Pick's disease. In another embodiment, the present invention provides a method of treating a subject with Lewy Body disease, comprising administering to the subject an omega-6 fatty acid or a metabolic precursor thereof, whereby the omega-6 fatty acid or metabolic precursor thereof increases a synthesis of a phospholipid by a neural cell or brain cell of the subject, thereby treating a subject with Lewy Body disease. In another embodiment, the present invention provides a method of treating a subject with Huntington's disease, comprising administering to the subject an omega-6 fatty acid or a metabolic precursor thereof, whereby the omega-6 fatty acid or metabolic precursor thereof increases a synthesis of a phospholipid by a neural cell or brain cell of the subject, thereby treating a subject with Huntington's disease. In another embodiment, the present invention provides a method of treating a subject with an MCI, comprising administering to the subject an omega-3 fatty acid or a metabolic precursor thereof, whereby the omega-6 fatty acid or metabolic precursor thereof increases a synthesis of a phospholipid by a neural cell or brain cell of the subject, thereby treating a subject with an MCI. Each possibility represents a separate embodiment of the present invention.

In another embodiment, the present invention provides a method of treating a subject with Pick's disease, comprising administering to the subject a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by a neural cell or brain cell of the subject, thereby treating a subject with Pick's disease. In another embodiment, the present invention provides a method of treating a subject with Lewy Body disease, comprising administering to the subject a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by a neural cell or brain cell of the subject, thereby treating a subject with Lewy Body disease. In another embodiment, the present invention provides a method of treating a subject with Huntington's disease, comprising administering to the subject a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by a neural cell or brain cell of the subject, thereby treating a subject with Huntington's disease. In another embodiment, the present invention provides a method of treating a subject with an MCI, comprising administering to the subject a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by a neural cell or brain cell of the subject, thereby treating a subject with an MCI. Each possibility represents a separate embodiment of the present invention.

In another embodiment, the present invention provides a method of treating a subject with Pick's disease, comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by a neural cell or brain cell of the subject, thereby treating a subject with Pick's disease. In another embodiment, the present invention provides a method of treating a subject with Lewy Body disease, comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by a neural cell or brain cell of the subject, thereby treating a subject with Lewy Body disease. In another embodiment, the present invention provides a method of treating a subject with Huntington's disease, comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by a neural cell or brain cell of the subject, thereby treating a subject with Huntington's disease. In another embodiment, the present invention provides a method of treating a subject with an MCI, comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by a neural cell or brain cell of the subject, thereby treating a subject with an MCI. Each possibility represents a separate embodiment of the present invention.

In another embodiment, the present invention provides a method of treating a subject with a vascular dementia, comprising administering to the subject a composition of the present invention, whereby the omega-3 fatty acid or metabolic precursor thereof increases a synthesis of a phospholipid by a neural cell or brain cell of the subject, thereby treating a subject with a vascular dementia.

In another embodiment, the present invention provides a method of treating a subject with an aging-related neurological disorder, comprising contacting a neural cell of the subject with a composition of the present invention, whereby the composition increases a synthesis of a phospholipid by the neural cell or brain cell, thereby treating a subject with an aging-related neurological disorder.

In another embodiment, the present invention provides a method of treating a subject with a symptom of depression, comprising contacting a neural cell of the subject with a composition of the present invention, whereby the composition increases a synthesis of a phospholipid by the neural cell or brain cell, thereby treating a subject with a symptom of depression. In another embodiment, the subject has a memory disorder. In another embodiment, the disorder is age-related. Each possibility represents a separate embodiment of the present invention.

In another embodiment, the symptom of depression is sadness. In another embodiment, the symptom of depression is reduced activity. In another embodiment, the symptom of depression is fatigue. In another embodiment, the symptom of depression is weakness. In another embodiment, the symptom of depression is mood fluctuations. In another embodiment, the symptom of depression is reduced concentration. In another embodiment, the symptom of depression is insomnia. In another embodiment, the symptom of depression is weight fluctuations. In another embodiment, the symptom of depression is reduced libido. In another embodiment, the symptom of depression is suicidal thoughts. Each symptom represents a separate embodiment of the present invention.

In another embodiment of methods and compositions of the present invention, the omega-3 fatty acid, omega-6 fatty acid, metabolic precursor thereof, or composition of the present invention exerts one of the effects enumerated herein by increasing a synthesis of a phospholipid. In another embodiment, the effect is manifested without increasing a synthesis of a phospholipid. Each possibility represents a separate embodiment of the present invention.

In another embodiment, methods and compositions of the present invention comprise a source of uridine. In another embodiment, methods and compositions of the present invention comprise a source of choline. In another embodiment, "source" refers to a compound that increases the concentration of the desired compound (uridine, choline, etc.) in the bloodstream or tissues. In another embodiment, "source" refers to a compound that is metabolized by a tissue or enzyme of the subject to the desired compound. In another embodiment, "source" refers to a compound that is metabolized by the target cell to the desired compound. In another embodiment, the uridine source is cytidine, which is converted into uridine by the human liver. In another embodiment, the uridine source is a cytidine 5' monophosphate. In another embodiment, the uridine source is a cytidine 5' diphosphate. In another embodiment, the uridine source is a cytidine 5' triphosphate. In another embodiment, the uridine source is any other cytidine phosphate known in the art. In another embodiment, the uridine source is a CDP-choline. In another embodiment, the uridine source is any other uridine source known in the art. Each uridine source represents a separate embodiment of the present invention. Each possibility represents a separate embodiment of the present invention.

The uridine phosphate utilized in methods of the present invention, is, in another embodiment, a uridine 5' monophosphate. In another embodiment, the uridine phosphate is a uridine 5' diphosphate. In another embodiment, the uridine phosphate is a uridine 5' triphosphate. In another embodiment, the uridine phosphate is any other uridine phosphate known in the art. Each possibility represents a separate embodiment of the present invention.

In other embodiments, uridine-based compounds other than uridine itself serve as uridine sources or uridine precursors. These are, in other embodiments, uridine-rich food or dietary products like algae; salts of uridine like uridine phosphates, acylated uridine or the like. In another embodiment, acyl derivatives of uridine or mixtures thereof, e.g. those disclosed in U.S. Pat. No. 5,470,838, are also administered. Each precursor of uridine represents a separate embodiment of the present invention.

In another embodiment, a method of the present invention further comprises administration of a choline. In another embodiment, the method further comprises administration of a choline salt. In another embodiment, the method further comprises administration of a compound that is metabolized into choline. In another embodiment, the method further comprises administration of a choline source. In another embodiment, administration of one of the above compounds augments the effect of the omega-3 or omega-6 fatty acid and/or uridine on synthesis of membrane phospholipids. As provided herein (Examples), administration of choline and an omega-3 or omega-6 fatty acid exhibit unexpected augmentation of levels of phospholipids, synaptic proteins, and synaptic membranes in neurons and brain tissue and of memory, intelligence, and cognitive and neurological functions.

In another embodiment, any of the methods and compositions of the present invention comprises administration of an omega-3 fatty acid and a choline. In another embodiment, any of the methods and compositions of the present invention comprise administration of an omega-3 fatty acid and a choline salt. In another embodiment, any of the methods and compositions of the present invention comprises administration of an omega-6 fatty acid and a choline. In another embodiment, any of the methods and compositions of the present invention comprises administration of an omega-6 fatty acid and a choline salt.

In another embodiment, any of the methods and compositions of the present invention comprises administration of a composition comprising an omega-3 fatty acid, a uridine, and a choline. In another embodiment, any of the methods and compositions of the present invention comprises administration of composition comprising an omega-3 fatty acid, a uridine, and a choline salt. In another embodiment, any of the methods and compositions of the present invention comprises administration of a composition comprising an omega-6 fatty acid, a uridine, and a choline. In another embodiment, any of the methods and compositions of the present invention comprises administration of composition comprising an omega-6 fatty acid, a uridine, and a choline salt.

In another embodiment, any of the methods and compositions of the present invention comprises administration of an omega-6 fatty acid and an omega-3 fatty acid. In another embodiment, any of the methods and compositions of the present invention comprises administration of an omega-6 fatty acid, an omega-3 fatty acid, and a uridine. In another embodiment, any of the methods and compositions of the present invention comprises administration of an omega-6 fatty acid, an omega-3 fatty acid, and a choline. In another embodiment, any of the methods and compositions of the present invention comprises administration of an omega-6 fatty acid, an omega-3 fatty acid, and a choline salt. In another embodiment, any of the methods and compositions of the present invention comprises administration of an omega-6 fatty acid, an omega-3 fatty acid, a uridine, and a choline. In another embodiment, any of the methods and compositions of the present invention comprises administration of an omega-6 fatty acid, an omega-3 fatty acid, a uridine, and a choline salt.

In another embodiment, an anti-inflammatory PUFA is included in methods and compositions of the present invention. In another embodiment, 2 different omega-3 fatty acids are included. In another embodiment, 1 of the 2 omega-3 fatty acids is an anti-inflammatory PUFA. In another embodiment, 1 of the 2 omega-3 fatty acids is DHA. In another embodiment, 1 of the 2 omega-3 fatty acids is EPA. In another embodiment, the 2 omega-3 fatty acids are EPA and DHA.

In another embodiment, the ratio of the 2 omega-3 fatty acids is 0.05:1. In another embodiment, is the ratio is 0.1:1. In another embodiment, is the ratio is 0.15:1. In another embodiment, is the ratio is 0.2:1. In another embodiment, is the ratio is 0.3:1. In another embodiment, is the ratio is 0.4:1. In another embodiment, is the ratio is 0.5:1. In another embodiment, is the ratio is 0.6:1. In another embodiment, is the ratio is 0.7:1. In another embodiment, is the ratio is 0.8:1. In another embodiment, is the ratio is 0.9:1. In another embodiment, is the ratio is 1:1. In another embodiment, DHA and EPA are included in one of the above ratios (DHA:EPA). In another embodiment, DHA and EPA are included in one of the above ratios (EPA:DHA).

In another embodiment, 2 different omega-6 fatty acids are included in methods and compositions of the present invention.

In another embodiment, the ratio of an omega-3 fatty acid to an omega-6 fatty in a method or composition of the present invention is 1:1. In another embodiment, the ratio is 1.5:1. In another embodiment, the ratio is 2:1. In another embodiment, the ratio is 3:1. In another embodiment, the ratio is 4:1. In another embodiment, the ratio is 5:1. In another embodiment, the ratio is 6:1. In another embodiment, the ratio is 8:1. In another embodiment, the ratio is 10:1. In another embodiment, the ratio is 12:1. In another embodiment, the ratio is 15:1. In another embodiment, the ratio is 20:1. In another embodiment, the ratio is 30:1. In another embodiment, the ratio is 40:1. In another embodiment, the ratio is 50:1. In another embodiment, the ratio is 60:1. In another embodiment, the ratio is 80:1. In another embodiment, the ratio is 100:1.

Each combination of an omega-3 fatty acid, an omega-6 fatty acid, a uridine, a choline, and/or a choline salt represents a separate embodiment of the present invention. Each combination of different omega-3 fatty acids represents a separate embodiment of the present invention. Each combination of different omega-6 fatty acids represents a separate embodiment of the present invention. Each ratio represents a separate embodiment of the present invention.

In another embodiment, the choline source is lecithin. In another embodiment, the choline source is a lecithin. In another embodiment, the choline source is an acetylcholine. In another embodiment, the choline source is a citicholine or an alpha-glycerophosphorylcholine. In another embodiment, the choline source is CDP-choline. In another embodiment, the choline source is any other choline source known in the art. Each choline source represents a separate embodiment of the present invention.

In another embodiment, the choline salt is a sulfonate salt; e.g a long-alkyl chain sulfonate salt. In another embodiment, the choline salt is choline chloride. In another embodiment, the choline salt is choline bitartrate. In another embodiment, the choline salt is choline citrate. In another embodiment, the choline salt is choline tartrate. In another embodiment, the choline salt is iron-choline citrate complex. In another embodiment, the choline source is any other choline salt known in the art. Each choline salt represents a separate embodiment of the present invention.

In another embodiment, the present invention provides a composition for the treatment of Alzheimer's disease, consisting of any of the compositions disclosed in methods of the present invention. Each composition represents a separate embodiment of the present invention.

In another embodiment, the present invention provides a composition for the treatment of memory impairment or memory loss, consisting of any of the compositions disclosed in methods of the present invention. Each composition represents a separate embodiment of the present invention. In addition, each type of memory impairment or memory loss represents a separate embodiment of the present invention.

In another embodiment, the present invention provides a composition for the treatment of Pick's disease, consisting of any of the compositions disclosed in methods of the present invention. In another embodiment, the present invention provides a composition for the treatment of Lewy Body disease, consisting of any of the compositions disclosed in methods of the present invention. In another embodiment, the present invention provides a composition for the treatment of Huntington's disease, consisting of any of the compositions disclosed in methods of the present invention. Each composition, and each of the above diseases, represents a separate embodiment of the present invention.

In another embodiment, methods and compositions of the present invention exert their effects even in subjects that do not have a deficiency in omega-3 fatty acids or omega-6 fatty acids. In another embodiment, a pharmacological dose of PUFA is utilized in methods and compositions of the present invention. In another embodiment, a therapeutic dose is utilized. In another embodiment, the pharmacological doses are greater than would normally be ingested in a PUFA-rich diet. In another embodiment, membrane levels of a subject not having a PUFA deficiency are increased by administration of pharmacological doses of PUFA and/or uridine. In another embodiment, results of the present invention demonstrate that PUFA exert a biochemical effect in the brain, thus supporting the use of pharmacological doses of PUFA. Each possibility represents a separate embodiment of the present invention.

The dosage of omega-3 fatty acid included in methods and compositions of the present invention is, in another embodiment, in the range of about 400-2000 mg/day. In another embodiment, the dosage is in the range of about 500-2000 mg/day. In another embodiment, the range is about 600-2000 mg/day. In another embodiment, the range is about 800-2000 mg/day. In another embodiment, the range is about 1000-2000 mg/day. In another embodiment, the range is about 1200-2000 mg/day. In another embodiment, the range is about 1500-2000 mg/day. In another embodiment, the range is about 400-3000 mg/day. In another embodiment, the dosage is in the range of about 500-3000 mg/day. In another embodiment, the range is about 600-3000 mg/day. In another embodiment, the range is about 800-3000 mg/day. In another embodiment, the range is about 1000-3000 mg/day. In another embodiment, the range is about 1200-3000 mg/day. In another embodiment, the range is about 1500-3000 mg/day. In another embodiment, the range is about 2000-3000 mg/day. In another embodiment, the range is about 400-4000 mg/day. In another embodiment, the dosage is in the range of about 500-4000 mg/day. In another embodiment, the range is about 600-4000 mg/day. In another embodiment, the range is about 800-4000 mg/day. In another embodiment, the range is about 1000-4000 mg/day. In another embodiment, the range is about 1200-4000 mg/day. In another embodiment, the range is about 1500-4000 mg/day. In another embodiment, the mange is about 2000-4000 mg/day. In another embodiment, the range is about 3000-4000 mg/day. In another embodiment, the range is about 400-1000 mg/day. In another embodiment, the range is about 500-1000 mg/day. In another embodiment, the range is about 600-1000 mg/day. In another embodiment, the range is about 800-100 mg/day.

In another embodiment, the dosage of omega-3 fatty acid is at least 400 mg/day. In another embodiment, the dosage is at least 500 mg/day. In another embodiment, the dosage is at least 600 mg/day. In another embodiment, the dosage is at least 700 mg/day. In another embodiment, the dosage is at least 800 mg/day. In another embodiment, the dosage is at least 900 mg/day. In another embodiment, the dosage is at least 1 g/day. In another embodiment, the dosage is at least 1200 mg/day. In another embodiment, the dosage is at least 1.5 g/day. In another embodiment, the dosage is at least 2 g/day.

In another embodiment, the dosage of omega-3 fatty acid is about 400 mg/day. In another embodiment, the dosage is about 500 mg/day. In another embodiment, the dosage is about 600 mg/day. In another embodiment, the dosage is about 700 mg/day. In another embodiment, the dosage is about 800 mg/day. In another embodiment, the dosage is about 900 mg/day. In another embodiment, the dosage is about 1 g/day. In another embodiment, the dosage is about 1200 mg/day. In another embodiment, the dosage is about 1.5 g/day. In another embodiment, the dosage is about 2 g/day.

In another embodiment, pregnant women are given a particular dosage to meet their needs. In another embodiment, the range is about 200-2000 mg/day. In another embodiment, the range is about 400-1700 mg/day. In another embodiment, the range is about 600-1500 mg/day. In another embodiment, the range is about 800-1300 mg/day. In another embodiment, the range is about 200-3000 mg/day. In another embodiment, the range is about 400-3000 mg/day. In another embodiment, the range is about 600-3000 mg/day. In another embodiment, the range is about 800-3000 mg/day. In another embodiment, the range is about 1000-3000 mg/day. In another embodiment, the range is about 2000-3000 mg/day. In another embodiment, the dosage for pregnant women is about 1000 mg/day. In another embodiment, the dosage is about 1500 mg/day. In another embodiment, the dosage is about 2000 mg/day. In another embodiment, the dosage is about 3000 mg/day.

In another embodiment, subjects with elevated cholesterol are given a particular dosage to meet their needs. In another embodiment, the dosage for subjects with elevated cholesterol is in the range of about 200-4000 mg/day. In another embodiment, the dosage for subjects with elevated cholesterol is in the range of about 400-3500 mg/day. In another embodiment, the dosage for subjects with elevated cholesterol is in the range of about 600-3000 mg/day. In another embodiment, the dosage for subjects with elevated cholesterol is in the range of about 1000-2500 mg/day. In another embodiment, the dosage for subjects with elevated cholesterol is in the range of about 1500-2300 mg/day. In another embodiment, the dosage for subjects with elevated cholesterol is about 2000 mg/day.

In another embodiment of methods and compositions of the present invention, DHA is included at one of the above doses. In another embodiment, the dosage of DHA is 1-50 mg/kg/day. In another embodiment, the dosage of DHA is 400-1000 mg/day. In another embodiment, EPA is included at one of the above doses. In another embodiment, the dosage of EPA is 1-50 mg/kg/day. In another embodiment, the dosage of EPA is 400-1000 mg/day. Each dosage represents a separate embodiment of the present invention.

The dosage of omega-6 fatty acid included in methods and compositions of the present invention is, in other embodiments, any of the dosages mentioned above for omega-3 fatty acid. In another embodiment, arachidonic acid is included at one of the above doses. In another embodiment, the dosage of arachidonic acid is 1-50 mg/kg/day. In another embodiment, the dosage of arachidonic acid is 400-1000 mg/day. Each dosage represents a separate embodiment of the present invention.

In another embodiment, eicosahexaenoic acid (EPA) is administered together with, or in addition to, another omega-3 or an omega-6 fatty acid. In another embodiment, the EPA is added in a dosage of about 200 mg/day. In another embodiment, the dosage is 100-300 mg/day. In another embodiment, the range is 150-250 mg/day. In another embodiment, the range is 170-230 mg/day. In another embodiment, the range is 100-1000 mg/day. In another embodiment, the range is 150-800 mg/day. In another embodiment, the range is 200-600 mg/day. In another embodiment, the range is 300-500 mg/day. In another embodiment, the dosage is about 300 mg/day. In another embodiment, the dosage is about 400 mg/day. In another embodiment, the dosage is about 500 mg/day. In another embodiment, the dosage is about 600 mg/day. In another embodiment, the dosage is about 800 mg/day. In another embodiment, the dosage is about 1000 mg/day.

In another embodiment, pregnant women are administered a higher dose of EPA. In another embodiment, the dosage is about 1200 mg/day. In another embodiment, the dosage is about 1500 mg/day. In another embodiment, the dosage is about 1800 mg/day. In another embodiment, the dosage is about 2000 mg/day. In another embodiment, the dosage is about 2500 mg/day. In another embodiment, the dosage is about 3000 mg/day. In another embodiment, the dosage is 500-3000 mg/day. In another embodiment, the dosage is 800-3000 mg/day. In another embodiment, the dosage is 1000-3000 mg/day. In another embodiment, the dosage is 1500-3000 mg/day. In another embodiment, the dosage is 2000-3000 mg/day. In another embodiment, the dosage is 500-2000 mg/day. In another embodiment, the dosage is 800-2000 mg/day. In another embodiment, the dosage is 1000-2000 mg/day. In another embodiment, the dosage is 1500-2000 mg/day.

Each dosage of an omega-3 fatty acid, an omega-6 fatty acid, or additional EPA represents a separate embodiment of the present invention.

The dose of uridine included in methods and compositions of the present invention, is, in another embodiment, between 10-500 mg/day (inclusive). In another embodiment, the dose is 20-500 mg/day. In another embodiment, the dose is 30-500 mg/day. In another embodiment, the dose is 50-500 mg/day. In another embodiment, the dose is 100-500 mg/day. In another embodiment, the dose is 150-500 mg/day. In another embodiment, the dose is 200-500 mg/day. In another embodiment, the dose is 300-500 mg/day. In another embodiment, the dose of uridine is between 10-400 mg/day. In another embodiment, the dose is 20-400 mg/day. In another embodiment, the dose is 30-400 mg/day. In another embodiment, the dose is 50-400 mg/day. In another embodiment, the dose is 100-400 mg/day. In another embodiment, the dose is 150-400 mg/day. In another embodiment, the dose is 200-400 mg/day. In another embodiment, the dose of uridine is between 10-300 mg/day. In another embodiment, the dose is 20-300 mg/day. In another embodiment, the dose is 30-300 mg/day. In another embodiment, the dose is 50-300 mg/day. In another embodiment, the dose is 100-300 mg/day. In another embodiment, the dose is 150-300 mg/day. In another embodiment, the dose is 200-300 mg/day. In another embodiment, the dose is about 50 mg/day. In another embodiment, the dose is about 70 mg/day. In another embodiment, the dose is about 100 mg/day. In another embodiment, the dose is about 150 mg/day. In another embodiment, the dose is about 200 mg/day. In another embodiment, the dose is about 300 mg/day. In another embodiment, the dose is about 400 mg/day. In another embodiment, the dose is about 500 mg/day.

Each uridine dose represents a separate embodiment of the present invention.

The dose of choline included in methods and compositions of the present invention, is, in another embodiment, between 100 mg-10 g/day (inclusive). In another embodiment, the dose is 1 g-3 g. In another embodiment, the dose is 150 mg-8 g. In another embodiment, the dose is 200 mg-6 g. In another embodiment, the dose is 300 mg-5 g. In another embodiment, the dose is 400 mg-4.5 g. In another embodiment, the dose is 500 mg-4 g. In another embodiment, the dose is 600 mg-4 g. In another embodiment, the dose is 800 mg-3.5 g. In another embodiment, the dose is 1.2 g-3 g. In another embodiment, the dose is 1.5 g-2.5 g. In another embodiment, the dose is about 0.5 g. In another embodiment, the dose is about 0.7 g. In another embodiment, the dose is about 1 g. In another embodiment, the dose is about 1.2 g. In another embodiment, the dose is about 1.5 g. In another embodiment, the dose is about 2 g. In another embodiment, the dose is about 2.5 g. In another embodiment, the dose is about 3 g. In another embodiment, the dose is about 4 g. Each of the above doses is the amount of choline equivalents; thus, the actual doses of a choline compound (e.g. choline chloride or choline tartrate) will be correspondingly greater.

Each choline dose represents a separate embodiment of the present invention.

In another embodiment, a composition of the present invention is administered chronically. "Chronically" refers, in another embodiment, to administration for at least 1 week. In another embodiment, the term refers to administration for at least 2 weeks. In another embodiment, the time period is at least 10 days. In another embodiment, the time period is at least 3 weeks. In another embodiment, the time period is at least 4 weeks. In another embodiment, the time period is at least 5 weeks. In another embodiment, the time period is at least 6 weeks. In another embodiment, the time period is at least 2 months. In another embodiment, the time period is at least 3 months. In another embodiment, the time period is at least 4 months. In another embodiment, the time period is at least 6 months. In another embodiment, the time period is at least 6 months. In another embodiment, the time period is at least 1 year. In another embodiment, the time period is at least 2 years. In another embodiment, the time period is at least 3 years. In another embodiment, the time period is at least 5 years. In another embodiment, the time period is at least 10 years.

In another embodiment, the time period is 1 week. In another embodiment, the term refers to administration for 2 weeks. In another embodiment, the time period is 10 days. In another embodiment, the time period is 3 weeks. In another embodiment, the time period is 4 weeks. In another embodiment, the time period is 5 weeks. In another embodiment, the time period is 6 weeks. In another embodiment, the time period is 2 months. In another embodiment, the time period is 3 months. In another embodiment, the time period is 4 months. In another embodiment, the time period is 6 months. In another embodiment, the time period is 6 months.

In another embodiment, the time period is 1 year. In another embodiment, the time period is 2 years. In another embodiment, the time period is 3 years. In another embodiment, the time period is 5 years. In another embodiment, the time period is 10 years.

In another embodiment, the PUFA component of a composition of the present invention is administered for one of the above time periods. In another embodiment, the omega-3 component of a composition of the present invention is administered for one of the above time periods. In another embodiment, the omega-6 component of a composition of the present invention is administered for one of the above time periods. In another embodiment, the uridine component of a composition of the present invention is administered for one of the above time periods. In another embodiment, the choline or choline salt component of a composition of the present invention is administered for one of the above time periods.

Each time period represents a separate embodiment of the present invention.

"Contacting," in another embodiment, refers to directly administering to the subject a composition of the present invention. In another embodiment, "contacting" refers to indirectly administering to the subject a composition of the present invention. Thus, in another embodiment, methods of the present invention include methods in which the subject is contacted with a compound or composition that is metabolized into an omega-3 or omega-6 fatty acid in the cerebrospinal fluid, the bloodstream, etc, after which the omega-3 or omega-6 fatty acid is brought in contact with the brain cell by diffusion or any other active transport or passive transport process known in the art by which compounds circulate within the body. In another embodiment, the compound is metabolized by the target cells into an omega-3 or omega-6 fatty acid. Each possibility represents a separate embodiment of the present invention.

In another embodiment, a derivative of an omega-3 or omega-6 fatty acid is utilized in the methods and compositions of the present invention. In another embodiment, the derivative is the omega-6 fatty acid derivative gamma-linolenic acid. In another embodiment, the derivative is any other derivative of an omega-3 or omega-6 fatty acid known in the art. Each derivative represents a separate embodiment of the present invention.

In another embodiment, the present invention provides a method of increasing neurite branching of a neural cell of a subject, comprising administering to the subject an omega-3 fatty acid or a metabolic precursor thereof, whereby the omega-3 fatty acid or metabolic precursor thereof increases a synthesis of a phospholipid by the neural cell, thereby increasing neurite branching thereof. In another embodiment, the present invention provides a method of increasing neurite branching of a neural cell of a subject, comprising administering to the subject an omega-6 fatty acid or a metabolic precursor thereof, whereby the omega-6 fatty acid or metabolic precursor thereof increases a synthesis of a phospholipid by the neural cell, thereby increasing neurite branching of a neural cell of a subject.

In another embodiment, the present invention provides a method of increasing neurite branching of a neural cell of a subject, comprising administering to the subject a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by the neural cell, thereby increasing neurite branching thereof. In another embodiment, the present invention provides a method of increasing neurite branching of a neural cell of a subject, comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by the neural cell, thereby increasing neurite branching of a neural cell of a subject.

In another embodiment, the present invention provides a method of increasing neurite outgrowth of a neural cell of a subject, comprising administering to the subject a composition comprising: (a) a uridine, an acyl derivative thereof, a uridine phosphate, or a CDP-choline; and (b) an omega-3 fatty acid or a metabolic precursor thereof, whereby the composition increases a synthesis of a phospholipid by the neural cell, thereby increasing neurite outgrowth thereof. In another embodiment, the present invention provides a method of increasing neurite outgrowth of a neural cell of a subject, comprising administering to the subject a composition comprising: (a) a uridine, an acyl derivative thereof, a uridine phosphate, or a CDP-choline; and (b) an omega-6 fatty acid or a metabolic precursor thereof, whereby the composition increases a synthesis of a phospholipid by the neural cell, thereby increasing neurite outgrowth of a neural cell of a subject.

In another embodiment, the present invention provides a method of increasing neurite outgrowth of a neural cell of a subject, comprising administering to the subject an omega-3 fatty acid or a metabolic precursor thereof, whereby the omega-3 fatty acid or metabolic precursor thereof increases a synthesis of a phospholipid by the neural cell, thereby increasing neurite outgrowth thereof. In another embodiment, the present invention provides a method of increasing neurite outgrowth of a neural cell of a subject, comprising administering to the subject an omega-6 fatty acid or a metabolic precursor thereof, whereby the omega-6 fatty acid or metabolic precursor thereof increases a synthesis of a phospholipid by the neural cell, thereby increasing neurite outgrowth of a neural cell of a subject.

In another embodiment, the present invention provides a kit comprising a compound or composition utilized in performing a method of the present invention.

"Pharmaceutical composition" refers, in another embodiment, to a dietary supplement. In another embodiment, the term refers to a nutritional supplement. In another embodiment, the term refers to a foodstuff of any sort that has been enriched with an omega-3 fatty acid. In another embodiment, the term refers to a foodstuff that has been enriched with an omega-6 fatty acid. In another embodiment, the term refers to a foodstuff that has been enriched with a uridine. In another embodiment, the term refers to a foodstuff that has been enriched with a choline. In another embodiment, the term refers to a foodstuff that has been enriched with a choline salt.

"Foodstuff" refers, in another embodiment, to a solid food. In another embodiment, the term refers to a drink. In another embodiment, the term refers to a powdered drink mix. In another embodiment, the term refers to a food-based preparation, functional food, dietary supplement or nutraceutical.

In another embodiment, a foodstuff can be of several forms including liquid, suspension, powder, semi-solid, and solid. Semi-solid is meant to include custards, dessert puddings, thick creams, mousses, parfaits, yogurts, and sweetened gelatins. Without limiting to particular embodiments, the solid form can be prepared as a bar similar to a energy bar, a chip, a cookie, a cracker, pasta or a puffed material, e.g. popcorn or a rice-cake-like foodstuff. Some embodiments require the individual to dissolve, suspend, or rehydrate the snack foodstuff.

Each type of pharmaceutical composition represents a separate embodiment of the present invention.

In another embodiment, the present invention relates to the use of an omega-3 or omega-6 fatty acid and/or its analog, derivative, isomer, metabolite, pharmaceutically acceptable salt, pharmaceutical product, hydrate, N-oxide, or a combination thereof. Thus, in another embodiment, the methods of the present invention comprise administering an analog of the PUFA. In another embodiment, the methods of the present invention comprise administering a derivative of the PUFA. In another embodiment, the methods of the present invention comprise administering an isomer of the PUFA. In another embodiment, the methods of the present invention comprise administering a metabolite of the PUFA. In another embodiment, the methods of the present invention comprise administering a pharmaceutically acceptable salt of the PUFA. In another embodiment, the methods of the present invention comprise administering a pharmaceutical product of the PUFA. IN another embodiment, the methods of the present invention comprise administering a hydrate of the PUFA. In another embodiment, the methods of the present invention comprise administering an N-oxide of the PUFA. In another embodiment, the methods of the present invention comprise administering any of a combination of an analog, derivative, isomer, metabolite, pharmaceutically acceptable salt, pharmaceutical product, hydrate or N-oxide of the PUFA.

In another embodiment of methods and compositions of the present invention, PUFA is administered as a triglyceride.

In another embodiment, the term "isomer" includes, but, in another embodiment, is not limited to, optical isomers and analogs, structural isomers and analogs, conformational isomers and analogs, and the like.

This invention further includes, in another embodiment, derivatives of a PUFA. The term "derivatives" includes but is not limited to ether derivatives, acid derivatives, amide derivatives, ester derivatives and the like. In addition, this invention further includes hydrates of the PUFA compounds. The term "hydrate" includes but is not limited to hemihydrate, monohydrate, dihydrate, trihydrate and the like.

This invention further includes metabolites of the PUFA compounds. The term "metabolite" means any substance produced from another substance by metabolism or a metabolic process.

This invention further includes pharmaceutical products of the PUFA compounds. The term "pharmaceutical product" means a composition suitable for pharmaceutical use (pharmaceutical composition), as defined herein.

In addition, the invention encompasses pure (Z)- and (E)-isomers of the PUFA compounds defined herein and mixtures thereof as well as pure (RR, SS)- and (RS, SR)-enantiomer couples and mixtures thereof.

Pharmaceutical Compositions and Methods of Administration

The pharmaceutical compositions containing the PUFA and/or uridine can be, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of PUFA and/or uridine over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the PUFA and/or uridine is released over a period of time after administration. Controlled- or sustained-release compositions include formulation in lipophilic depots (e.g. fatty acids, waxes, oils). In another embodiment, the composition is an immediate-release composition, i.e. a composition in which all the PUFA and/or uridine is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the therapeutic target, e.g. the brain, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the PUFA and/or uridine or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the PUFA and/or uridine or their physiologically tolerated derivatives such as salts, esters, N-oxides, and the like are converted into a solution, suspension, or emulsion, if desired with the substances customary and suitable for this purpose, for example, solubilizers or other substances.

An active component is, in another embodiment, formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Each of the above additives, excipients, formulations and methods of administration represents a separate embodiment of the present invention.

EXPERIMENTAL DETAILS SECTION

Example 1

Treatment of PC-12 Cells with Omega-3 Fatty Acids Increases Phospholipid Synthesis Materials and Experimental Methods Reagents $^{14}$C-labeled choline chloride was obtained from Perkin-Elmer (Boston, Mass.). DHA, oleic acid, or palmitic acid were obtained from Biomol, (Plymouth Meeting, Pa.). $^{14}$C-choline was obtained from Amersham Biosciences Corp (Piscataway, N.J.).

Cell Culture

PC-12 cells were maintained in Dulbecco's modified Eagle's medium (DMEM)+10% fetal bovine serum (FBS). For experiments, cells were grown in quintuplicate collagen-coated 35 millimeter (mm) dishes. Cells were incubated for 18 hours (hr) in serum-free DMEM containing 28 µM choline+/−5 micromolar (µM) of DHA, oleic acid, or palmitic acid. Cells were then labeled for 2.5 hr with 0.5 microcurie (µCi)/ml $^{14}$C-choline in serum-free DMEM containing 10-micromolar (µM) choline.

Quantification of Labeled Phospholipids

Cells were homogenized in 100 volumes of ice-cold deionized water using a tissue degrader (Polytron PT 10-35, Kinematica A G, Switzerland); 1 ml of aliquots were then mixed with 3 ml of chloroform+methanol mixture (2:1 v/v) and vortexed vigorously for 30 seconds. After cooling for 1 h on ice, the mixture was mixed sequentially with 3 ml of chloroform+methanol mixture (2:1 v/v) and 1 ml of ice-cold deionized water. The mixture was vortexed vigorously and allowed to stand overnight in the cold room (18 h). The organic (lower) and aqueous (upper) phases of the mixtures were separated by centrifugation (10 min at 4° C.; 1000 g). An aliquot (2 ml) of the upper phase was used for determination of CDP-Choline (see below), and 0.1-0.4 ml aliquots of the lower phase were dried under vacuum for phospholipid analysis. Residues of 0.1 ml aliquots of the lower phase were assayed for total phospholipid content by measuring phosphorus. Residues of 0.4 ml aliquots of the lower phase were reconstituted in 40 µl methanol and subjected to thin-layer chromatography using silica G plates (Adsorbosil Plus-1®, Alltech), and a system consisting of chloroform/ethanol/triethylamine/water (30:34:30:8) as the mobile phase. Phospholipid standards were used to identify the corresponding bands under UV light after the plates were sprayed with 0.1% diphenylhexatriene in petroleum ether. Bands for individual phospholipid classes (PC, PE, SM, PS and PI) were scraped off the plates and extracted into 1 ml of methanol; dried under vacuum; and assayed for phosphorus content. Total phosphorus was determined by comparison with standard curves by using $KH_2PO_4$ run with each assay. To each sample was added 0.5 ml of 4.5% $HclO_4$/27% $H_2SO_4$ and tubes were heated at 180° C. for 3 h. After cooling to room temperature, 5 ml of the color reagent (a 10:1 dilution of solutions containing 2.5 mg/ml ammonium molybdate, 8.2 mg/ml sodium acetate and 100 mg/ml ascorbic acid respectively) was added and the tubes were incubated for 2 h, 37° C. Absorbance was measured spectrophotometrically at 820 nm. Phospholipid mass was determined by multiplying the phosphorus content by 25.

Statistical Analysis

Data were analyzed by one-way ANOVA (analysis of variance), followed by Student's t test.

Results

In order to assess the effect of omega-3 fatty acids on phospholipid synthesis, PC-12 cells were incubated with $^{14}$C-labeled choline, following an 18-hour pre-incubation with or without DHA. Incorporation of label into phospholipids was then measured. Oleic acid and palmitic acid, which are not omega-3 fatty acids, were used as negative controls. Phosphatidylcholine (PC) synthesis was significantly increased by pre-incubation with DHA, but not oleic acid or palmitic acid, as evidenced by increased incorporation of the label into PC (FIG. 1). Thus, treatment with omega-3 fatty acids increases cellular phospholipid synthesis.

Example 2

Figure 2:
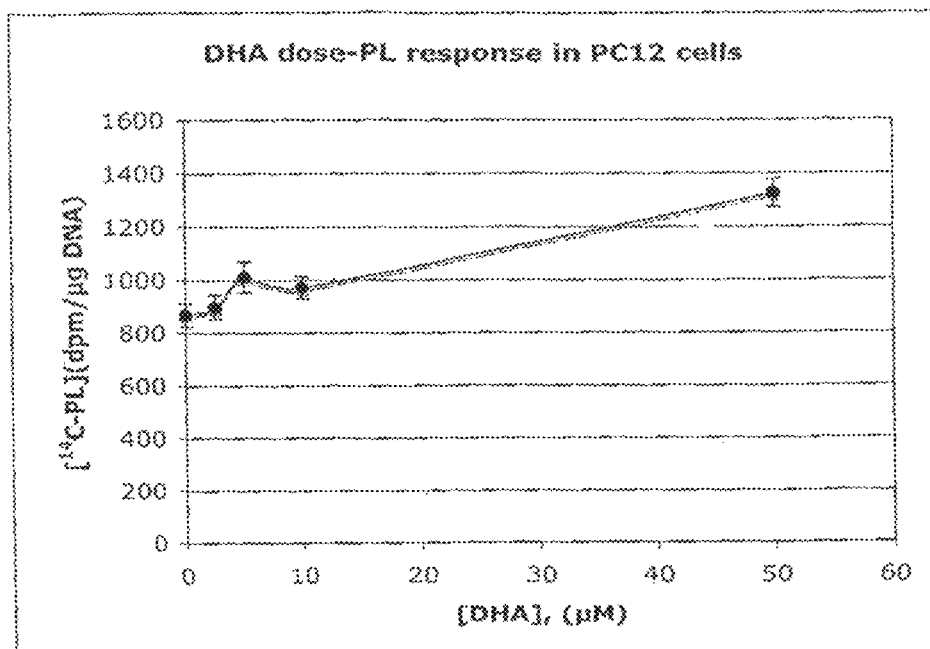
FIG. 2: DHA augmentation of phospholipid synthesis is dose-dependent. *-p<0.05. **-p<0.001.

Omega-3 Fatty Acids Increase Synthesis of a Number of Phospholipids in a Dose-Dependent Fashion To further characterize the stimulation of phospholipid synthesis by omega-3 fatty acids, PC-12 cells were pre-treated with different doses of DHA and exposed to labeled choline as described in Example 1, then incorporation of $^{14}$C-label into phospholipids was measured. Pre-treatment with DHA increased synthesis of phospholipids (FIG. 2). The augmentation of synthesis was dose-dependent. Thus, omega-3 fatty acids stimulate phospholipid synthesis in a dose-dependent manner.

Example 3

Treatment of SHSY-5Y Cells with Omega-6 Fatty Acids Increases Phospholipid Synthesis Materials and Experimental Methods Cell Culture SHSY-5Y cells were grown to near confluency in DMEM+10% FBS in 35 mm dishes. Cells were incubated for 18 hr in serum-free DMEM+1% FBS containing 30 µM choline+/−10 µM of DHA, arachidonic acid, or palmitic acid. Cells were then labeled, and labeled phospholipids were quantified as described for Example 1.

Preparation of DHA-BSA Complex

DHA was dissolved in ethanol to a 100 micromolar concentration and frozen in 10 microliter aliquots at −80° C. For each experiment, one aliquot was diluted in ethanol to 10 micromolar; the volume giving the desired final solution in incubation medium was mixed with an equal volume of BSA solution (1 gm/ml).

Results

Figure 3A:
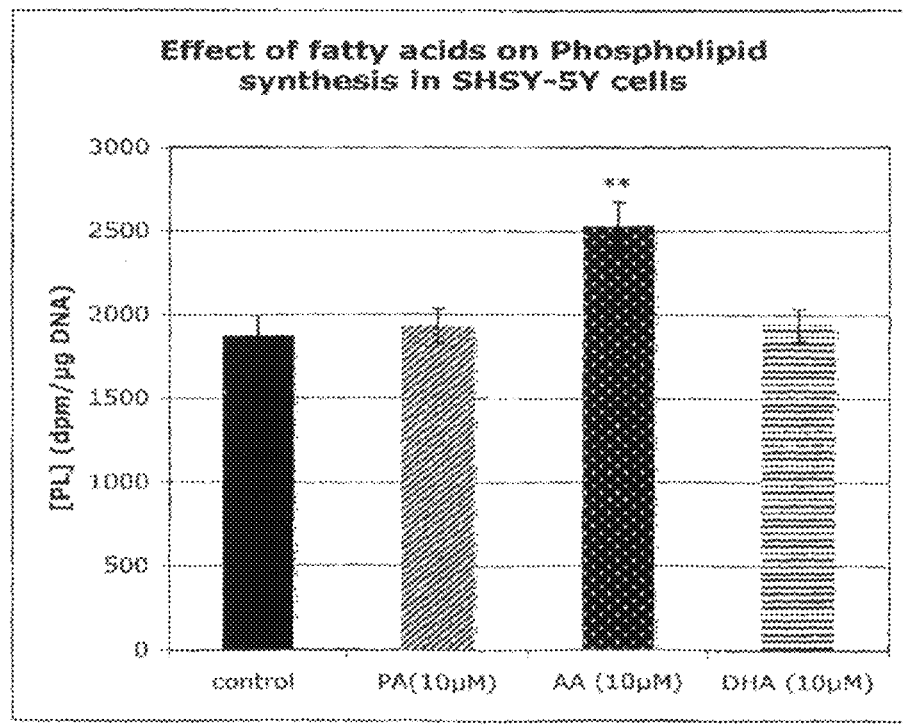
FIG. 3. A. Arachidonic acid increases phospholipid synthesis in SHSY-5Y cells. DHA: docosahexaenoic acid. AA: arachidonic acid. PA: palmitic acid. *: p<0.05. **: p<0.001. B. AA augmentation of phospholipid synthesis is dose-dependent.

The effect of omega-6 fatty acids on phospholipid synthesis was next examined in SHSY-5Y cells, a human neuroblastoma cell line. In this case, phospholipid synthesis was enhanced by arachidonic acid, an omega-6 fatty acid, but not by DHA or palmitic acid (FIG. 3A).

Example 4

Figure 3B:
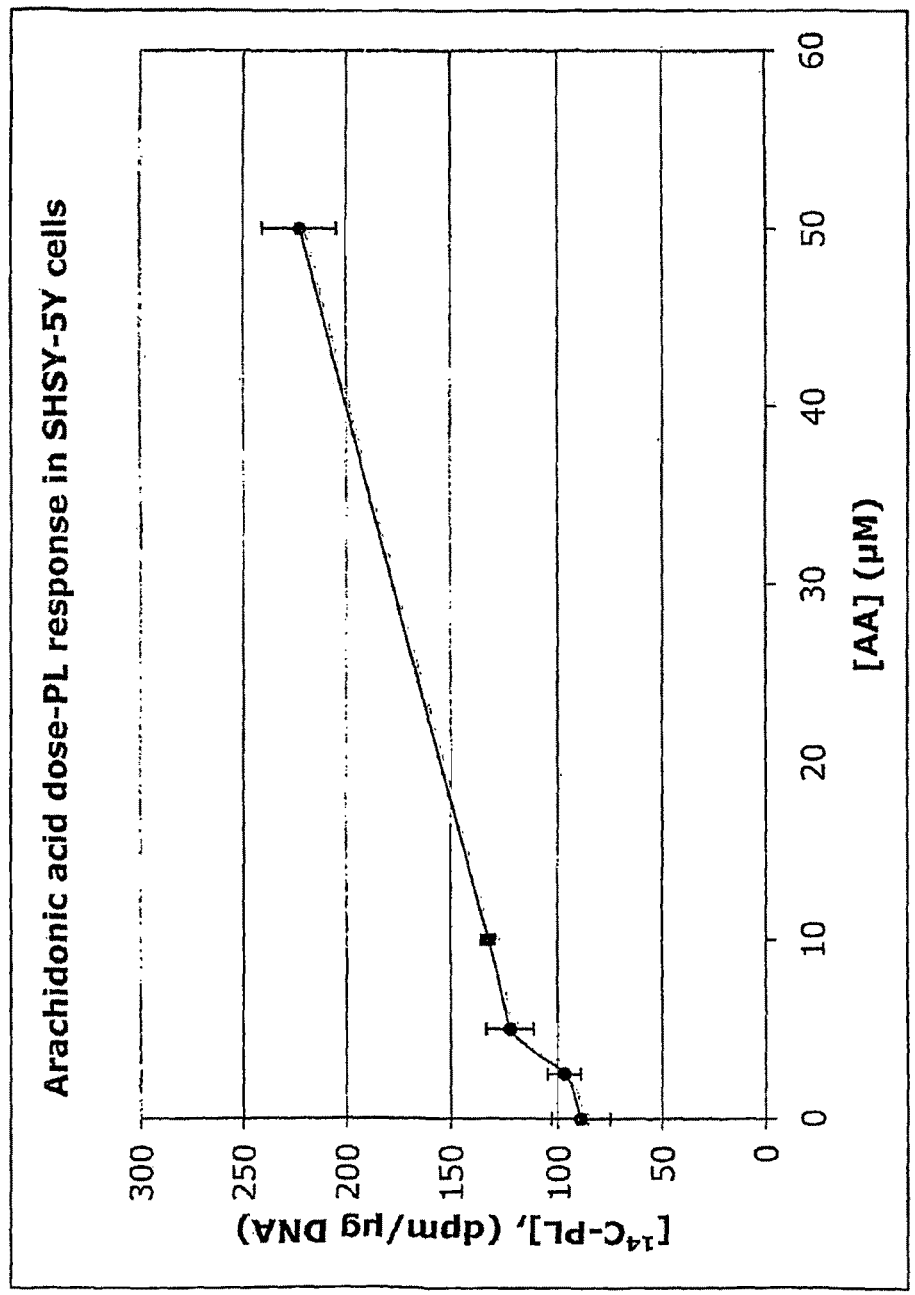

Omega-6 Fatty Acids Increase Synthesis of a Number of Phospholipids in a Dose-Dependent Fashion The effect of arachidonic acid on phospholipid synthesis in SHSY-5Y cells was further characterized as described for omega-3 fatty acids and PC-12 cells in Example 2. Arachidonic acid increased synthesis of total phospholipids, PC, and phosphatidylethanolamine over a range of dosages in a dose-dependent manner, as seen for DHA (FIG. 3B). Thus, omega-6 fatty acids stimulate synthesis of a variety of phospholipids in a dose-dependent manner.

Example 5

Administration of PUFA Increases Brain Phospholipid Levels, and Addition of Uridine Results in a Further Synergistic Increase Materials and Experimental Methods Diets Control standard diet (Table 4) consisted of Teklad Global 16% protein rodent diet (Harlan Teklad, Madison, Wis.), which contained 0.1% choline chloride (CC), corresponding to a daily dose of 50 mg/kg/day. UMP was provided as 0.5% UMP.2Na$^+$ weight/weight, added to the control diet, also prepared by Harlan Teklad, corresponding to 240 mg/kg/day UMP. DHA was administered as 300 mg/kg/day in 200 microliter (mcL)/day 5% Arabic Gum solution, while groups not receiving DHA were administered vehicle (5% Arabic Gum) alone. DHA was provided by Nu-Chek Prep (Elysian, Minn.) and UMP by Numico (Wagenigen, NL). None of the groups exhibited significant changes in body weight during the course of the experiment.

TABLE 4

Control standard diet.

| Proximate analysis (%) | |
|---|---|
| Protein | 16.7% |
| Carbohydrate | 60.9% |
| Oil, fiber, ash | 13.7% |
| Choline | 0.1% |
| Fatty acids (g/kg) | |
| Saturated | 7.34 |
| Unsaturated | |
| C18:1n-9 oleic acid | 8.96 |
| C18:2n-6 linoleic acid | 23.12 |
| C18:3n-3 linolenic acid | 1.53 |

Brain Harvesting

Gerbils were anesthetized with ketamine and xylazine (80 and 10 mg/kg bwt, i.p.) and sacrificed by immersing the head into liquid nitrogen for 2 min, followed by decapitation. Brains were immediately and quickly (30 seconds) removed using a bone rongeur and stored at −80° C.

Brain Phospholipid Measurements

Frozen brain hemispheres were weighed and homogenized in 100 volumes of ice-cold deionized water using a tissue degrader (Polytron PT 10-35, Kinematica A G, Switzerland), then analyzed as described in Example 1.

DNA and Protein Assays

Protein in whole brain homogenate sample was measured for using bicinchoninic acid reagent (Perkin Elmer, Norwalk, Conn., USA). DNA was measured by measuring 460 nm emission of samples on a fluorometer in the presence of bisbenzimidizole, a fluorescent dye known as Hoechst H 33258 (American Hoechst Corporation), which has an excitation maximum at 356 nm and an emission maximum of 458 when bound to DNA.

Results

Male gerbils weighing 80-100 g were divided into 4 groups of 8 gerbils and administered the supplements depicted in Table 1:

TABLE 1

Treatment groups.

| Group | Supplement | Amount/method |
|---|---|---|
| 1 | Control diet + vehicle (5% arabic gum) | |
| 2 | sodium UMP + vehicle (5% arabic gum) | Na-UMP 0.5% of chow. |
| 3 | DHA | 300 mg/kg daily by gavage |
| 4 | DHA + sodium UMP | As above |

Figure 4:
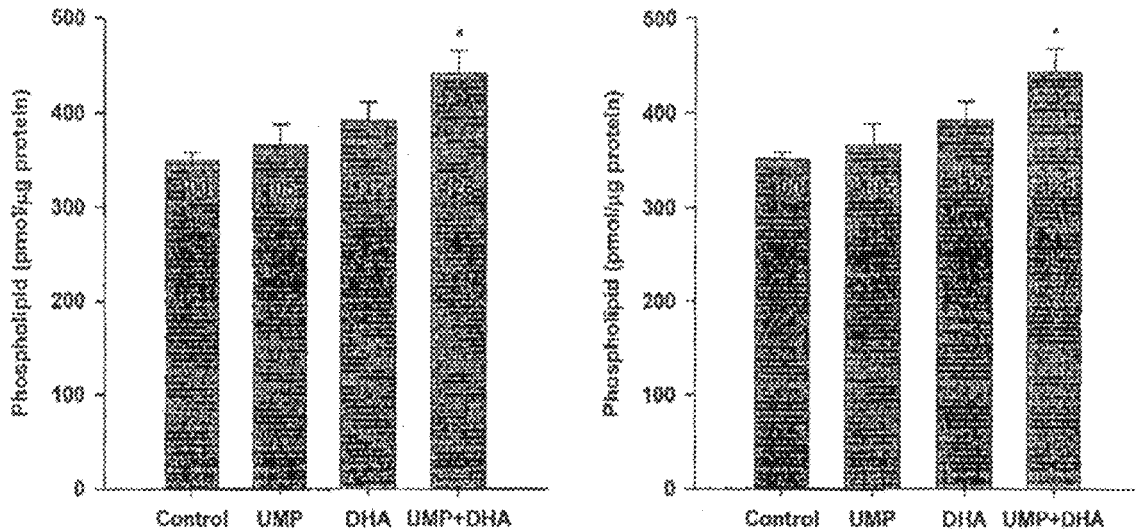
FIG. 4. DHA and UMP synergize to increase brain phospholipid levels in a whole-animal study. "*": significantly higher than control group by one-way ANOVA. A. pmol phospholipid per milligrams (mg) protein. UMP+DHA was significantly higher than control (p<0.05) (one-way ANOVA [F(3,28)=4.12; p=0.015]). Two-way ANOVA revealed statistically significant effect of DHA as well, relative to the control group [F(1,28)=8.78; p=0.006]. B. pmol phospholipid per μg DNA. UMP+DHA was significantly higher than control (p=0.020) (one-way ANOVA [F(3,28)=3.215; p=0.038]).
Figure 4:
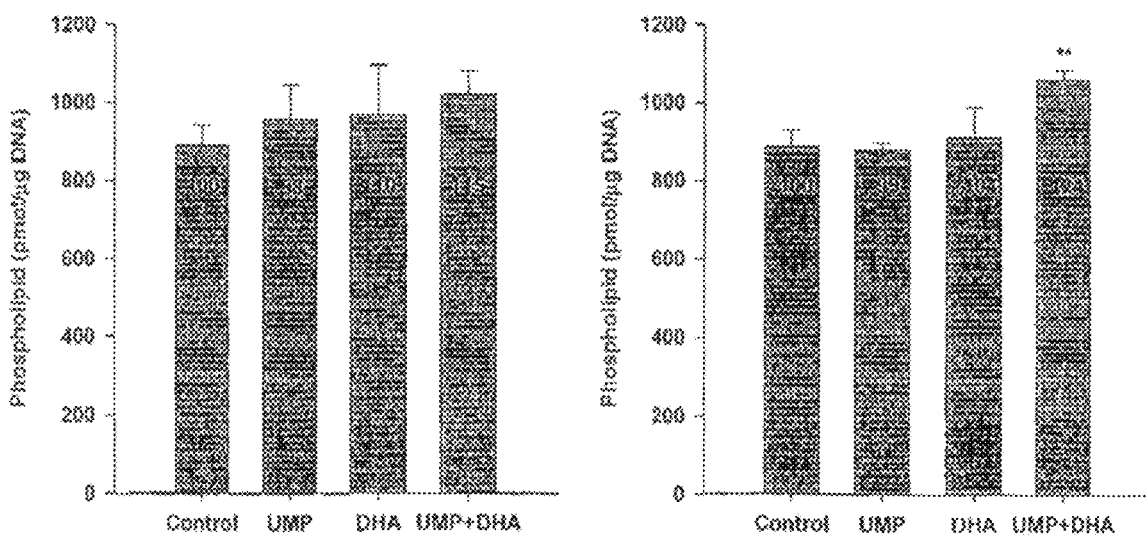

After 4 weeks, animals were sacrificed, and 1 hemisphere of the brain, minus the cerebellum and brain stem, was assayed for total phospholipids, and content of PC, phosphatidylethanolamine (PE) sphingomyelin (SM), phosphatidylinositol (PI), and phosphatidylserine (PS). Omega-3 fatty acids (DHA) increased levels of total phospholipids to levels significantly above the control group (FIG. 4 and Tables 2 and 3). Combination of DHA with UMP resulted in a further increase (26%) that was synergistic (i.e. greater than the sum of the increases observed in the DHA (12%) and UMP (5%) groups). Similar results were observed with each individual phospholipid (Tables 2 and 3). Statistical significance was observed whether phospholipid values were normalized to amounts of protein (FIG. 4 A and Table 2) or to DNA (FIG. 4 B and Table 3).

TABLE 2

Effects of DHA, UMP, or both treatments on brain phospholipid levels, normalized to protein levels. Data are presented as mean +/− standard error of the mean (SEM). Statistical analysis utilized two-way ANOVA and Tukey test.

| Treatment | Lipid | | | | | |
|---|---|---|---|---|---|---|
| | Total PL | PC | PE | SM | PS | PI |
| Control | 351 ± 8 | 152 ± 6 | 64 ± 4 | 45 ± 2 | 33 ± 3 | 21 ± 2 |
| UMP | 367 ± 22 | 171 ± 8* | 84 ± 8* | 52 ± 5 | 35 ± 3 | 31 ± 2** |
| DHA | 392 ± 20 | 185 ± 12* | 78 ± 5* | 56 ± 3* | 39 ± 3 | 32 ± 2** |
| UMP + DHA | 442 ± 24*** | 220 ± 12*** | 113 ± 6*** | 73 ± 4*** | 46 ± 6*** | 36 ± 6*** |

*indicates P < 0.05;

**P < 0.01;

***P < 0.001 relative to control group.

TABLE 3

Effects of DHA, UMP, or both treatments on brain phospholipid levels, normalized to DNA levels. Statistical analysis/data presentation are as in Table 2.

| Treatment | Total PL | PC | PE | SM | PS | PI |
|---|---|---|---|---|---|---|
| | | | Lipid | | | |
| Control | 885 ± 45 | 332 ± 12 | 176 ± 13 | 112 ± 5 | 79 ± 8 | 54 ± 5 |
| UMP | 878 ± 18 | 368 ± 10* | 195 ± 9 | 111 ± 4 | 86 ± 7 | 78 ± 6** |
| DHA | 909 ± 77 | 366 ± 13* | 196 ± 18 | 126 ± 8 | 98 ± 7 | 84 ± 13** |
| UMP + DHA | 1058 ± 25*** | 462 ± 26*** | 261 ± 30*** | 169 ± 11*** | 110 ± 5*** | 85 ± 10*** |

These findings confirm the results of the above Examples, showing that both omega-3 fatty acids and omega-6 fatty acids increase brain phospholipid synthesis and brain phospholipid levels, both total levels and those of individual phospholipids. These findings further show that combination of PUFA with uridine results in further synergistic increases. In addition, these findings show that stimulation of phospholipid synthesis by PUFA is a general phenomenon, not restricted to a particular phospholipid or experimental model.

The proportional increases in the 4 structural phospholipids that comprise the bulk of cellular membranes in the brain (the 4 phosphatides: PC, PE, PS, and sphingomyelin) were approximately equal, with levels of each of these four compounds rising by about 20%. Thus, the proportions of the 4 structural phospholipids in the membranes were maintained. Accordingly, membrane mass was increased without disrupting the normal membrane structure and function. These findings corroborate the data from previous Examples, providing further evidence that compositions of the present invention improve and enhance brain function.

Example 6

Administration of Omega-3 Fatty Acids to Gerbils Decreases Brain CDP-Choline Levels while Increasing Those of Brain Phospholipids Materials and Experimental Methods CDP-Choline Assay Aliquots (2 ml) of the upper (aqueous) phase were dried under a vacuum, reconstituted, and injected into an HPLC. The dried samples were reconstituted in 100-200 μl water and were analyzed by HPLC on an anion exchange column (Alltech Hypersil APS-2, 5 mm, 250×4.6 mm). CDP-choline was eluted with a linear gradient of buffers A ($H_3PO_4$, 1.75 mM, pH 2.9) and B ($NaH_2PO_2$, 500 mM, pH 4.5) from 0 to 100% B over period of 30 min. With this system, CDP-choline was resolved from closely co-eluting substances such as UMP in an isocratic system over a period of 40 min. The retention time for CDP-choline was 9.5 min. The column was washed with buffer B at the end of each experiment and every several days to remove retained nucleotides. Individual nucleotide peaks were detected by UV absorption at 280 nm and were identified by comparison with the positions of authentic standards, as well as by the addition of nucleotide standards to samples.

Results

Figure 5:
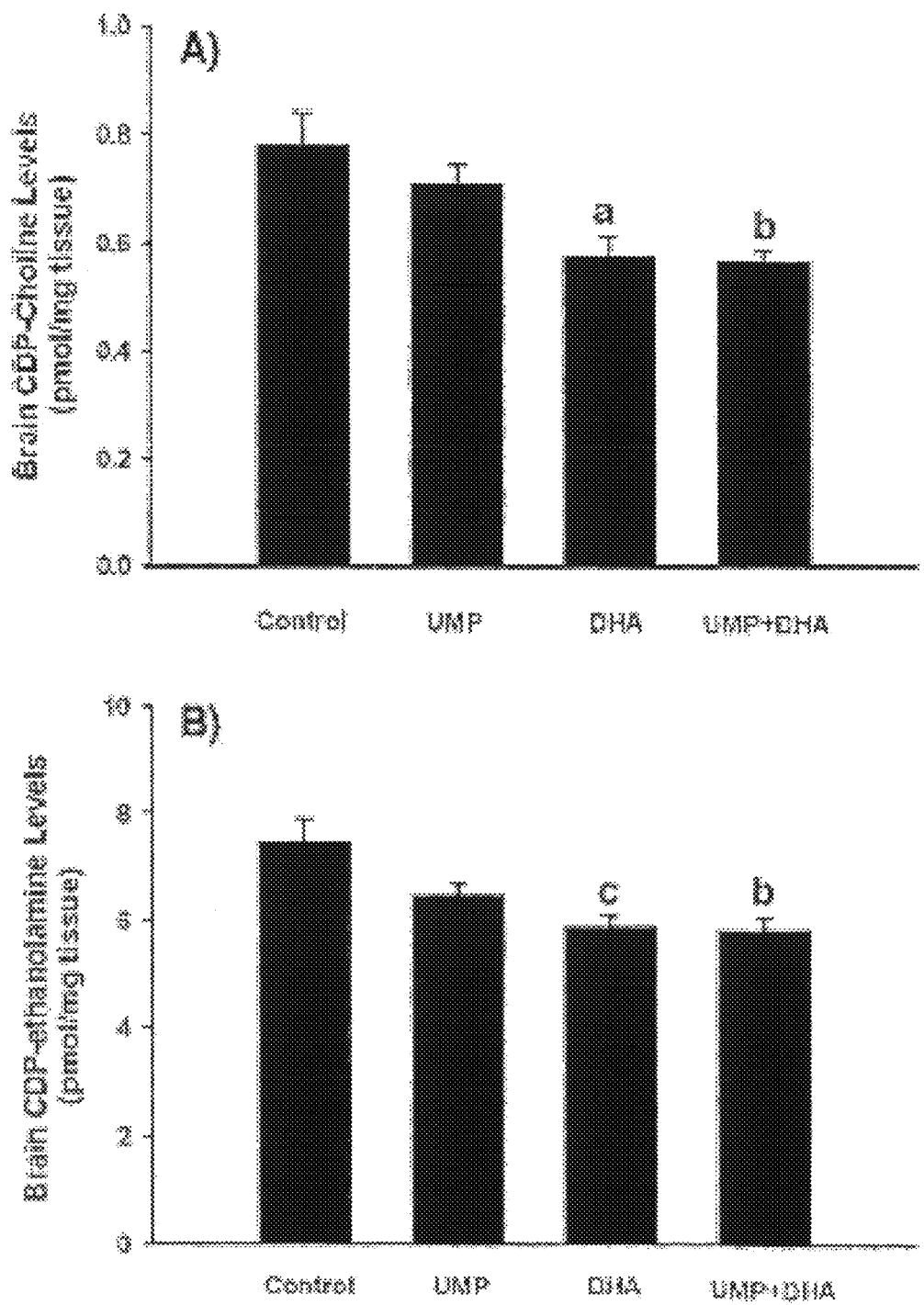
FIG. 5. Effects of DHA on brain CDP-choline levels (A) and CDP-ethanolamine levels (B). Groups of 8 gerbils received either a control or a UMP-containing diet, and, by gavage, DHA (in a vehicle of 5% gum Arabic solution) or 5% gum Arabic solution alone for 28 days. On the 29th day brains were harvested and assayed for CDP-choline. Data are presented as means±SEM. Statistical analysis was performed using one- or two-way ANOVA followed by Tukey test. a: P<0.05 when compared with the values for control diet plus vehicle group; b: P<0.05 when compared with values for UMP diet plus vehicle group.

To determine the effect of PUFA administration on CDP-choline levels, brain CDP-choline levels were measured in the animals from the previous Example. Administration of DHA and/or UMP decreased CDP-choline levels (FIG. 5A) and CDP-ethanolamine levels (FIG. 5B). DHA reduced CDP-choline levels by 26% (compared with those receiving just the control diet and DHA's vehicle), and in UMP-treated gerbils by 21% (compared with those receiving UMP-containing diet and DHA's vehicle) (both $P<0.05$). Two-way ANOVA revealed a significant effect of DHA [$F(1,28)=31.7$; $P<0.001$].

In another study, addition of UMP to the standard diet without concurrent DHA treatment significantly increased brain levels of PC, PE and PI by 13%, 29% and 48%, respectively (Table 5A). Administration of DHA without UMP also significantly increased brain levels of these phosphatides (by 22%, 20% and 52%, respectively), as well as of sphingomyelin (by 24%). UMP+DHA increased all of the phospholipids by more than the sum of the increases produced by UMP or DHA alone.

Next, the time course of these increases was examined. After 1 week of treatment, UMP produced no significant effects, while UMP+DHA caused small but significant increases in brain PC (21%) and PS (38%). Treatment with UMP+DHA for 3 weeks caused significant increases (21-48%) in all 5 of the phospholipids; UMP alone caused smaller but still significant increases (Table 5B).

TABLE 5

Effects and UMP and/or PUFA on brain phospholipid levels.

| Treatments (groups) | Total PL (nmol/mg prt) | PtdCho (nmol/mg prt) | PtdEtn (nmol/mg prt) | SM (nmol/mg prt) | PtdSer (nmol/mg prt) | PtdIns (nmol/mg prt) |
|---|---|---|---|---|---|---|
| A | | | | | | |
| Control diet + Vehicle | 351 ± 8 | 152 ± 6 | 65 ± 4 | 45 ± 2 | 33 ± 3 | 21 ± 2 |
| UMP diet + Vehicle | 367 ± 22 | 171 ± 8* | 84 ± 8* | 52 ± 5 | 35 ± 3 | 31 ± 2** |
| Control diet + DHA | 392 ± 20 | 185 ± 12* | 78 ± 5* | 56 ± 3* | 39 ± 3 | 32 ± 2** |
| UMP diet + DHA | 442 ± 24*** | 220 ± 12*** | 113 ± 6*** | 73 ± 4*** | 46 ± 6*** | 36 ± 3*** |

TABLE 5-continued

Effects and UMP and/or PUFA on brain phospholipid levels.

| Treatments (groups) | Total PL (nmol/mg prt) | PtdCho (nmol/mg prt) | PtdEtn (nmol/mg prt) | SM (nmol/mg prt) | PtdSer (nmol/mg prt) | PtdIns (nmol/mg prt) |
|---|---|---|---|---|---|---|
| B | | | | | | |
| Control + Vehicle | 403 ± 23 | 155 ± 8 | 69 ± 3 | 47 ± 3 | 34 ± 1 | 20 ± 2 |
| One week | | | | | | |
| UMP + Vehicle | 390 ± 21 | 154 ± 6 | 63 ± 4 | 49 ± 3 | 39 ± 1 | 20 ± 4 |
| UMP + DHA | 435 ± 15 | 188 ± 8* | 79 ± 6 | 57 ± 6 | 47 ± 1*** | 23 ± 1 |
| Three weeks | | | | | | |
| UMP + Vehicle | 479 ± 6** | 199 ± 5*** | 87 ± 4* | 70 ± 4* | 42 ± 2* | 25 ± 1 |
| UMP + DHA | 502 ± 12*** | 217 ± 5*** | 102 ± 4*** | 73 ± 5** | 41 ± 1* | 27 ± 1* |

Thus, under these conditions, the effect of PUFA administration on brain phospholipids is attributable to increased conversion of CDP-choline to PC and related phosphatides.

Example 7

Administration of Omega-3 Fatty Acids and/or Uridine to Gerbils Increases Levels of Synaptic Proteins Materials and Experimental Methods Synaptic Protein Level Assays Synaptic proteins were assayed by Slot-Blot and by Western Blot. For Western blotting, the aliquots of brain homogenates were mixed with 2×KFL loading buffer and boiled for 5 minutes prior to gel electrophoresis. Equal amounts of protein were loaded and separated using SDS-PAGE (4-20%; Bio-Rad, Hercules, Calif., USA). Proteins were then transferred onto PVDF membranes (Immobilon-P, Millipore, Billerica, Mass., USA). The remaining binding sites were blocked with 4% non-fat dry milk (Varnation, Glendale, Calif., USA) for 30 min in Tris-buffered saline-Tween (TBST). 2×KFL loading buffer was prepared by combining: 3.76 ml of 1M TRIS, pH 6.8; 6 ml of 20% sodium dodecyl sulfate; 6 ml of glycerol; 1.5 ml of mercaptoethanol; 2 ml of 1% bromphenol blue; and 10.74 ml of water.

For slot blotting, two sets of aliquots (18-21 μl; containing 20 μg of protein) from brain homogenates in deionized water were blotted directly onto polyvinylidene difluoride membranes (Immobilon-P, Millipore, Billerica, Mass., USA) by vacuum filtration, using a slot-blot microfiltration apparatus [Minifold® II Slot Blot System (SCR 072/0); Schleicher & Schuell, Inc., Keene, N.H., USA]. Remaining binding sites were blocked with 4% non-fat dry milk (Varnation, Glendale, Calif., USA) for 30 min in TBST. Membranes (from slot blots and Western blots) were then rinsed 5 times in TBST buffer and immersed in TBST solution containing the antibody of interest (mouse anti-NF-70, rabbit anti-NF-M, mouse anti-PSD-95 and mouse anti-synapsin-1). Following overnight incubation and five rinses in TBST buffer, blots were incubated for 1 h with the appropriate peroxidase-linked secondary antibody. Blots were then rinsed in TBST buffer five times, and protein-antibody complexes were detected and visualized using the ECL system (Amersham Biosciences, Piscataway, N.J., USA) and Kodak X-AR film. Films were digitized using a Supervista S-12 scanner with a transparency adapter (UMAX Technologies, Freemont, Calif., USA). Immuno-reactive bands were compared by densitometry using the Public Domain NIH Image program. Areas under the absorbance curve were normalized as percentages of those generated in control groups in the same blot. Protein levels expressed as the percent of these in control animals.

Results

Figure 6:
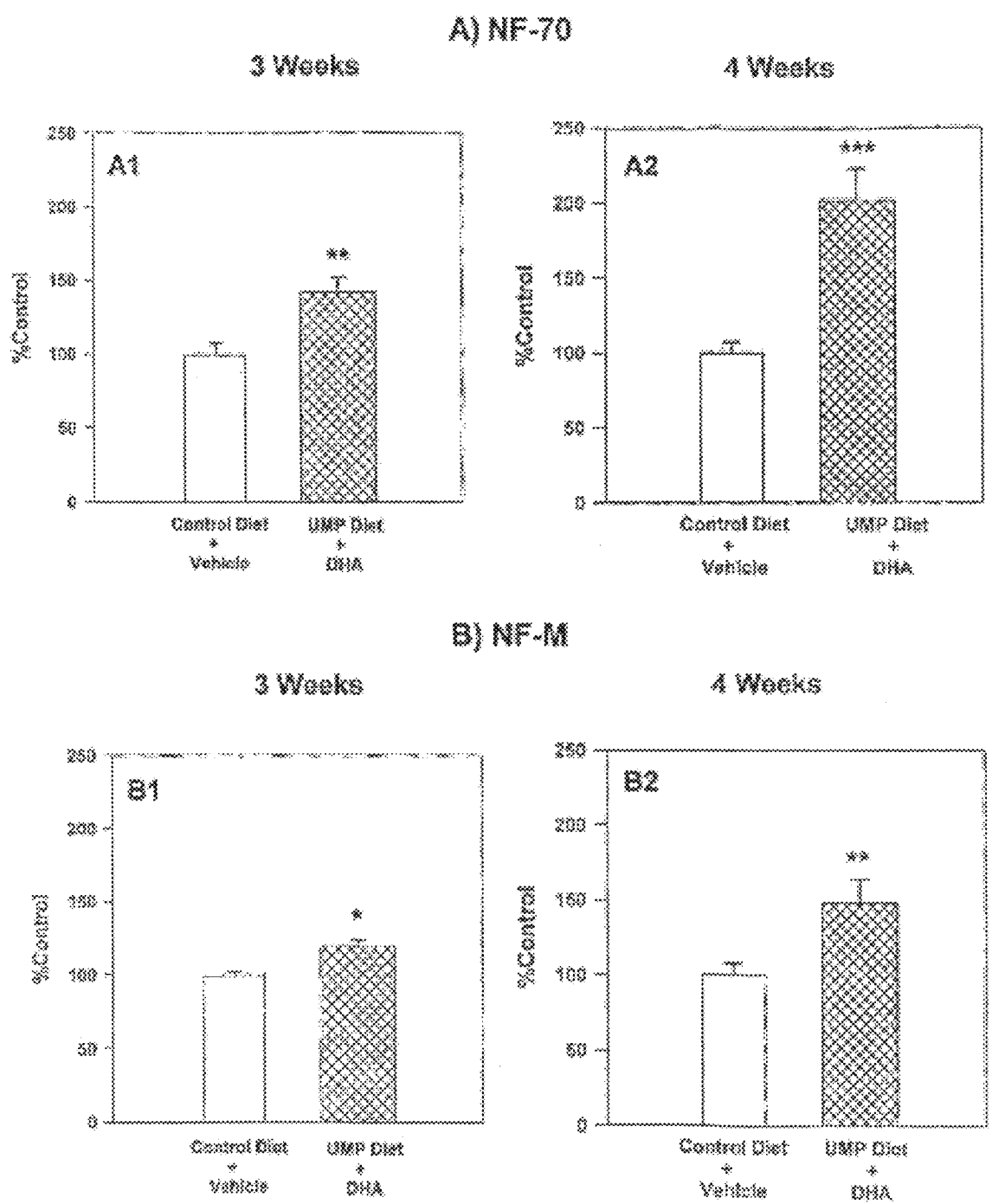
FIG. 6. Effects of UMP diet and DHA on brain NF-70 (A) and NF-M (B) levels Gerbils received the diets described in the FIG. 5 legend for 21 (left panels) or 28 (right panels) days. On the 22nd and 29th days, brains were harvested and assayed for NF-70. Values are depicted as mean±SEM. Statistical analysis was performed using one-way ANOVA and Tukey test. A. : P<0.01; *: P<0.001 compared to values for control diet+vehicle group. B). *P<0.05; **P<0.01. No significant differences in levels of the cytoskeletal protein beta-tubulin were observed between groups.
Figure 7:
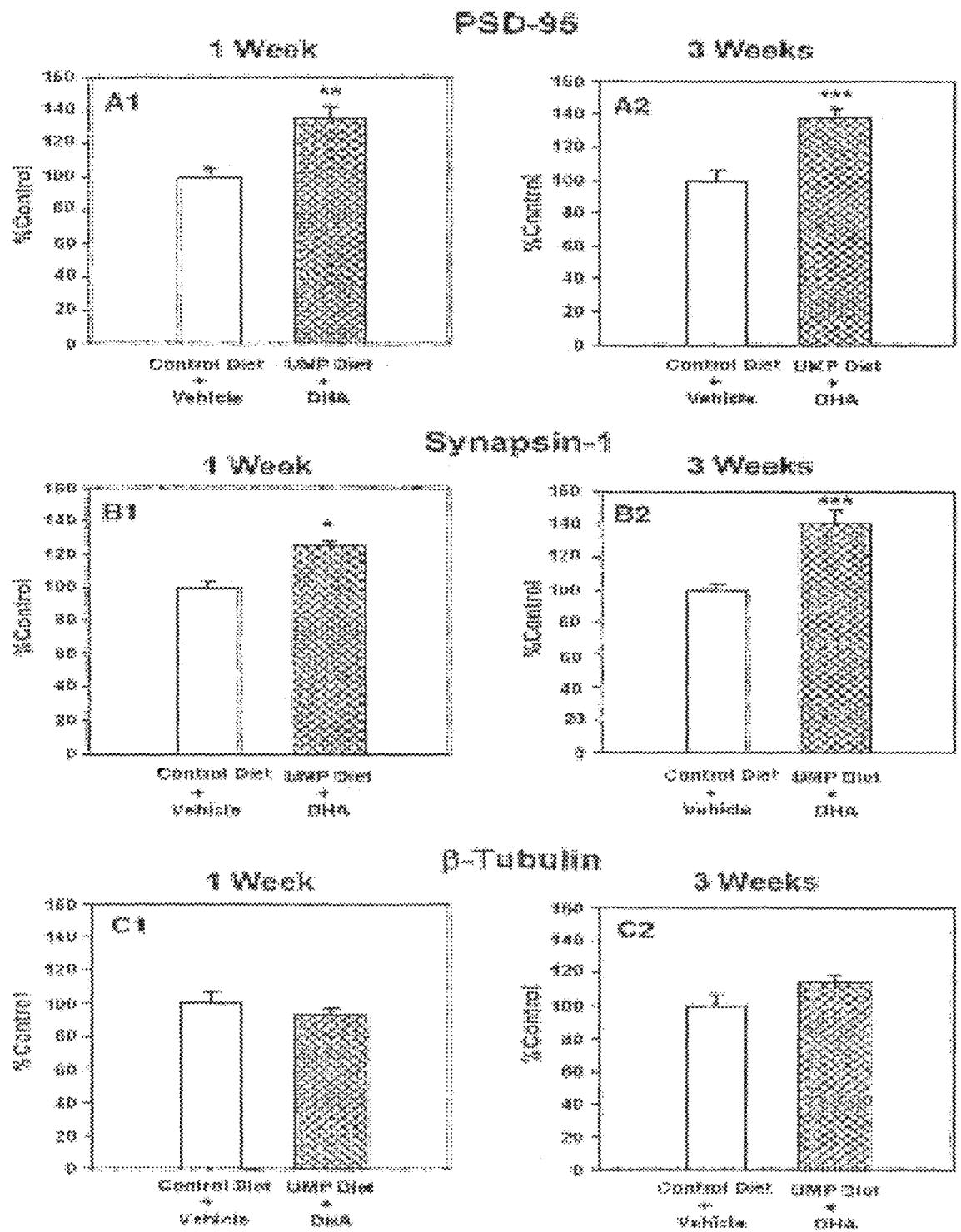
FIG. 7. Effects of UMP diet and DHA on brain PSD-95 and Synapsin-1 levels. A) Gerbils received either a control diet plus, by gavage, 5% gum Arabic, or a UMP-containing (0.5%) diet plus, by gavage, DHA (300 mg/kg) dissolved in the vehicle for 7 (left panels) or 21 (right panels) days. On the following day, brains were harvested and assayed for PSD-95 (A) or Synapsin-1 (B). A. Values represent means±SEM. Statistical analysis was performed using one-way ANOVA followed by Tukey test. P<0.01; *P<0.001 when compared with values for control diet plus vehicle group. B). *P<0.05; **P<0.01.

Brain levels of 4 synaptic proteins were measured in animals (n=8) receiving both UMP and DHA in the amounts described in Example 5. After 3 or 4 weeks of treatment, the neurite neurofibrillar proteins NF-70 and NF-M rose by 43% ($P<0.01$) or 102% ($P<0.001$), and by 19% ($P<0.05$) or 48% ($P<0.01$), respectively (FIG. 6). Levels of the postsynaptic density protein PSD-95 and the vesicular protein Synapsin-1 rose by 38% and 41% after 3 weeks (both $P<0.001$) and by 35% ($P<0.01$) or 25% ($P<0.05$) after 1 week (FIG. 7).

These findings provide further evidence that administration of PUFA and uridine increases the quantity of synaptic membranes. These increases were similar to those observed in phospholipid levels, showing that synapse levels were increased in the brain.

Example 8

DHA, EPA, and AA Increase Brain Phospholipid Levels

Materials and Experimental Methods

Adult gerbils were administered control standard diet (Table 4) with our without 0.5% UMP and/or 300 mg/kg/day DHA, EPA, or AA. Groups not receiving DHA were administered vehicle (5% Arabic Gum) alone.

Results

Gerbils were administered UMP and/or PUFA for 3 weeks and sacrificed, and brain levels of various phospholipid were measured. As shown in Table 6, DHA, EPA, and AA all increased phospholipid levels.

TABLE 6

Brain phospholipid levels following administration of PUFA and/or uridine.

| Treatment | Total PL | PC | PE | SM | PS | PI |
|---|---|---|---|---|---|---|
| Ctrl + vehicle | 333 ± 9 | 113 ± 6 | 63 ± 4 | 19 ± 1 | 25 ± 2 | 15 ± 1 |
| UMP + vehicle | 332 ± 5 | 131 ± 2 | 70 ± 1 | 22 ± 1 | 29 ± 1 | 16 ± 1 |

TABLE 6-continued

Brain phospholipid levels following administration of PUFA and/or uridine.

| Treatment | Total PL | PC | PE | SM | PS | PI |
|---|---|---|---|---|---|---|
| Ctrl + DHA | 344 ± 16 | 133 ± 6 | 77 ± 2 | 24 ± 2 | 34 ± 3 | 18 ± 2 |
| Ctrl + EPA | 347 ± 19 | 125 ± 8 | 76 ± 4 | 26 ± 3 | 31 ± 1 | 22 ± 2 |
| UMP + DHA | 374 ± 17 | 147 ± 6 | 88 ± 3 | 28 ± 3 | 39 ± 2 | 22 ± 2 |
| UMP + EPA | 407 ± 22 | 148 ± 3 | 91 ± 4 | 30 ± 1 | 41 ± 2 | 26 ± 2 |
| UMP + AA | 389 ± 28 | 127 ± 8 | 88 ± 10 | 25 ± 2 | 31 ± 3 | 22 ± 2 |

Example 9

Figure 8:
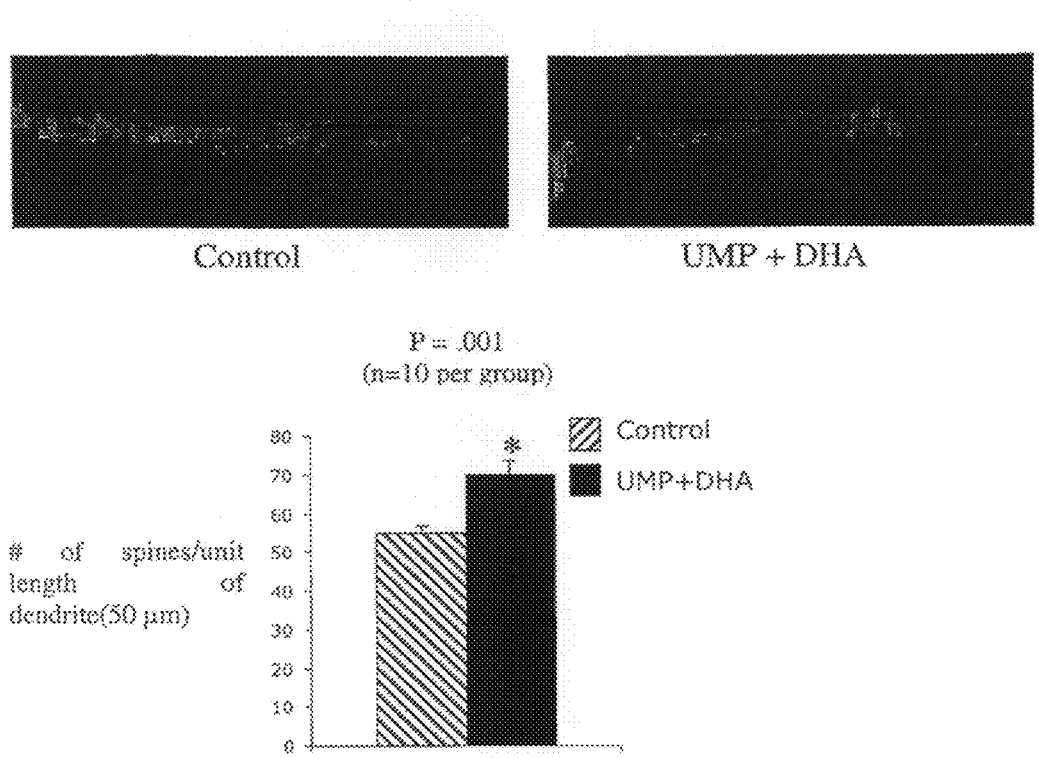
FIG. 8. Increased dendritic spine density in adult gerbil hippocampus.

Omega-3 Fatty Acids and Uridine Increase Numbers of Dendritic Spines in Adult and Developing Gerbil and Rat Brains Normal adult gerbils were given a control diet or a diet supplemented with UMP (240 mg uridine/kg) and DHA (300 mg/kg, by gavage) daily for up to 2 weeks. Animals were decapitated, and fixed hippocampal slices were stained with the carbanocyanine membrane tracer DiI(C18)3 ("DiI," Molecular Probes, Eugene, Oreg.) at the end of the treatment. Images of hippocampal neurons were obtained by two-photon microcopy. In animals receiving the DHA+UMP, dendritic spine density (number of spines per unit length of dendrite) increased significantly in hippocampal CA1 pyramidal neurons (27% increase, p=0.001 vs. control group; (FIG. 8).

In another study, pregnant rats were allowed to consume ad libitum, for 10 days before parturition and 20 days while nursing, either a choline-containing control diet or this diet supplemented with uridine as UMP; half of each group also received DHA or its diluent daily, by gavage. Pups were then sacrificed and brain slices were examined to determine numbers of hippocampal dendritic spines. UMP alone and DHA alone each increased levels of dendritic spine numbers, while the combination resulted in further increases (Table 7).

TABLE 7

Increases in dendritic spine numbers in developing animals in response to UMP and DHA administration.

| Treatment | Number of spines | Increase over control (%) |
|---|---|---|
| Control | 53 | — |
| UMP | 68 | 28% |
| DHA | 70 | 32% |
| UMP + DHA | 75 | 42% |

Example 10

DHA and UMP Improve Learning

Materials and Experimental Methods

Food and water were available ad libitum until the day of experimental testing, at which point gerbils were first fasted for 17 hours overnight and then provided with food from 11 AM to 6 PM. Gerbils ate UMP-supplemented chow and/or 300 mg/kg DHA from 3 months of age (n=8 per group), 4 weeks prior to behavioral training, until the end of the training period. Animals were first handled daily for 4 days to habituate them to routine contact. They were familiarized with the maze for an additional 4 days by placing food pellets throughout the arms and allowing 3 min for exploration. Gerbils received 1 trial/day, and all surfaces were sanitized with 10% ethanol between trials. Training consisted of placing a food pellet at the distal end of all the same 2 arms for all trials. The gerbil was placed in the center of the maze and allowed 2 min to find the food pellets. Working memory errors occurred whenever a gerbil re-entered an arm which contained a food pellet and which had previously been visited during a trial. Reference memory errors occurred whenever a gerbil entered an arm that had not contained a food pellet during previous trials. The percent of food pellets found was recorded.

Results

Figure 9:
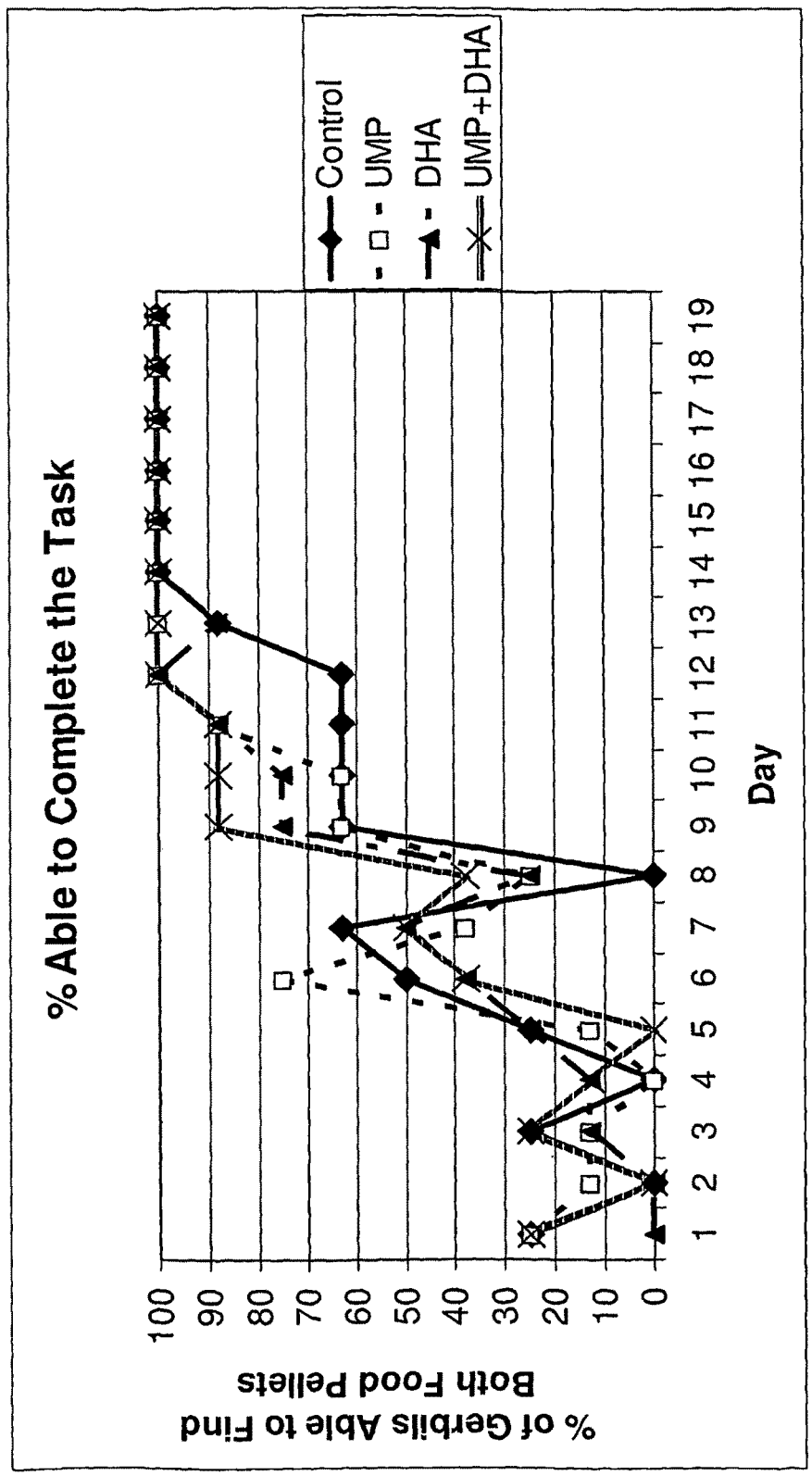
FIG. 9. Effect of uridine and/or DHA on learning.

To determine the effect of uridine and/or DHA on learning, animals administered uridine and/or DHA containing diets and then subjected to a memory test. DHA and UMP improved the percentage of animals able to complete the task (FIG. 9).

Example 11

Omega-3 Fatty Acids Increase Phospholipid Synthesis in Neurons in Short-Term Culture Materials and Experimental Methods Rat hippocampal cells were cultured for 3 weeks in Neutrobasal plus B27 medium, to reach full maturation. On the day of the experiment, cells were incubated with DMEM+choline, with or without added DHA. $^{14}$C-choline was added, cells were incubated for an additional 2 h, and newly-formed $^{14}$C-labeled PC was extracted and measured as described in Example 1.

Results

Figure 10:
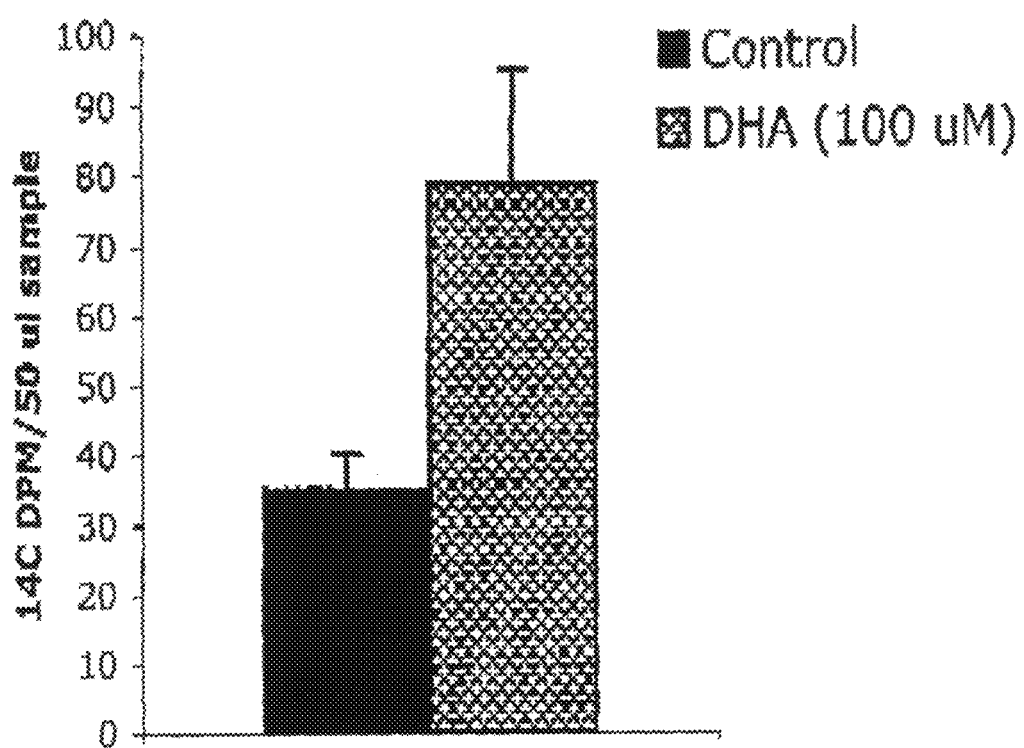
FIG. 10. Effect of DHA on phospholipid synthesis in cultured hippocampal neurons. Vertical axis: $^{14}C$ DPM/50 µl sample.

To determine the effect of DHA on phospholipids in neurons in short-term culture, neurons were pre-treated with DHA+choline. DHA increased synthesis of phospholipids relative to cells administered choline alone ("control") more than 2-fold (FIG. 10; P=0.04). These findings confirm that DHA increases phospholipid levels in brain and neural cells.

What is claimed is:

1. A method of increasing an amount of a synaptic membrane of a neural cell or brain cell of a subject comprising
administering to said subject in need of such treatment a therapeutically effective amount of a composition having:
(a) an omega-3 fatty acid, an omega-6 fatty acid, or a combination thereof;
(b) uridine, an acyl derivative thereof, a uridine phosphate or a CDP-choline; and
(c) a choline salt,
wherein uridine, an acyl derivative thereof, a uridine phosphate or CDP-choline is dosed to provide a range of 10 to 500 mg of uridine per day and choline is dosed in a range of 100 mg to 10 g per day.

2. The method of claim 1, wherein said subject has a memory disorder selected from the group consisting of Alzheimer's disease, Pick's disease, Lewy Body disease, Huntington's disease and mild cognitive impairment.

3. The method of claim 1, whereby the composition increases a synthesis of a phospholipid in a neural cell or brain cell of said subject.

4. The method of claim 3, wherein said phospholipid is a phosphatidylcholine, a phosphatidylethanolamine, a phosphatidylinositol, a phosphatidylserine, or a sphingomyelin.

5. The method of claim 1, wherein said omega-3 fatty acid is docosahexaenoic acid, eicosapentaenoic acid, alpha-linolenic acid, or a combination thereof.

6. The method of claim 1, wherein said omega-6 fatty acid is arachidonic acid, linoleic acid, or a combination thereof.

7. The method of claim 1, wherein said uridine phosphate is a uridine-5'-monophosphate (UMP), uridine-5'-diphosphate (UDP), uridine-5'-triphosphate (UTP), or is a salt of said UMP, UDP or UTP.

8. The method of claim 7, wherein said uridine phosphate is a uridine-5'-monophosphate (UMP).

9. The method of claim 1, wherein the choline salt is choline chloride, choline bitartrate or choline stearate.

10. The method of claim 1, wherein the composition is a medicament or nutritional supplement.

11. The method of claim 1, wherein the composition comprises between about 200 mg and about 800 mg of a choline salt.

12. The method of claim 1, wherein the composition comprises uridine-5'-monophosphate (UMP), a choline salt and docosahexaenoic acid.

13. A method of increasing a size or number of synapses in a brain of a subject, comprising
administering to said subject in need of such treatment a therapeutically effective amount of a composition comprising
(a) an omega-3 fatty acid, an omega-6 fatty acid, or a combination thereof;
(b) uridine, an acyl derivative thereof, a uridine phosphate or a CDP-choline, and
(c) a choline salt,
wherein uridine, an acyl derivative thereof, a uridine phosphate or CDP-choline is dosed to provide a range of 10 to 500 mg of uridine per day and choline is dosed in a range of 100 mg to 10 g per day.

14. The method of claim 13, wherein said subject has a memory disorder selected from the group consisting of Alzheimer's disease, Pick's disease, Lewy Body disease, Huntington's disease and mild cognitive impairment.

15. The method of claim 13, whereby the composition increases a synthesis of a phospholipid in a neural cell or brain cell of said subject.

16. The method of claim 15, wherein said phospholipid is a phosphatidylcholine, a phosphatidylethanolamine, a phosphatidylinositol, a phosphatidylserine, or a sphingomyelin.

17. The method of claim 13, wherein said omega-3 fatty acid is docosahexaenoic acid, eicosapentaenoic acid, alpha-linolenic acid, or a combination thereof.

18. The method of claim 13, wherein said omega-6 fatty acid is arachidonic acid, linoleic acid, or a combination thereof.

19. The method of claim 13, wherein said uridine phosphate is a uridine-5'-monophosphate (UMP), uridine-5'-diphosphate (UDP), uridine-5'-triphosphate (UTP), or is a salt of said UMP, UDP or UTP.

20. The method of claim 19, wherein said uridine phosphate is a uridine-5'-monophosphate (UMP).

21. The method of claim 13, wherein the choline salt is choline chloride, choline bitartrate or choline stearate.

22. The method of claim 13, wherein the composition is a medicament or nutritional supplement.

23. The method of claim 13, wherein the composition comprises between about 200 mg and about 800 mg of a choline salt.

24. The method of claim 13, wherein the composition comprises uridine-5'-monophosphate (UMP), a choline salt and docosahexaenoic acid.

* * * * *

UNITED STATES PATENT AND TRADEMARK OFFICE
CERTIFICATE OF CORRECTION

| | | |
|---|---|---|
| PATENT NO. | : 10,525,071 B2 | Page 1 of 1 |
| APPLICATION NO. | : 11/920914 | |
| DATED | : January 7, 2020 | |
| INVENTOR(S) | : Wurtman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 938 days.

Signed and Sealed this
Twenty-eighth Day of October, 2025

John A. Squires
*Director of the United States Patent and Trademark Office*